(12) United States Patent
Barry et al.

(10) Patent No.: US 11,679,177 B2
(45) Date of Patent: Jun. 20, 2023

(54) POLYMERIC COMPOSITIONS, DELIVERY DEVICES, AND METHODS

(71) Applicants: BAXTER INTERNATIONAL INC., Deerfield, IL (US); BAXTER HEALTHCARE S.A., Glattpark (CH)

(72) Inventors: John Barry, Buffalo Grove, IL (US); Paul Sanders, Greendale, WI (US); Rahul Singh, Milwaukee, WI (US); Krishnakumarsinh H. Parmar, Lisle, IL (US); Ben Ko, Cincinnati, OH (US); Stephanie Klunk, Liberty Township, OH (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 1279 days.

(21) Appl. No.: 16/041,238

(22) Filed: Jul. 20, 2018

(65) Prior Publication Data
US 2019/0046683 A1   Feb. 14, 2019

Related U.S. Application Data

(60) Provisional application No. 62/581,453, filed on Nov. 3, 2017, provisional application No. 62/542,615, filed on Aug. 8, 2017.

(51) Int. Cl.
*A61M 35/00* (2006.01)
*A61B 17/00* (2006.01)
(Continued)

(52) U.S. Cl.
CPC .... *A61L 26/0038* (2013.01); *A61B 17/00491* (2013.01); *A61L 26/008* (2013.01);
(Continued)

(58) Field of Classification Search
CPC .... A61M 5/2033; A61M 5/3015; A61M 5/19; A61M 5/20; A61M 5/24; A61M 5/3202;
(Continued)

(56) References Cited

U.S. PATENT DOCUMENTS 2,507,244 A   5/1950   Correll
3,583,399 A   6/1971   Ritsky
(Continued)

FOREIGN PATENT DOCUMENTS

CN    1251049    4/2000
CN    1287890    3/2001
(Continued)

OTHER PUBLICATIONS

International Preliminary Report on Patentability dated Feb. 24, 2020 for PCT/US2018/058500 (16 pages).
(Continued)

*Primary Examiner* — Erich G Herbermann
*Assistant Examiner* — Linnae E. Raymond
(74) *Attorney, Agent, or Firm* — K&L Gates LLP

(57) ABSTRACT

Polymeric compositions, methods, and delivery devices for inhibiting bleeding are disclosed. The method includes applying a dried material topically to a wound site, where the material may include a cross-linked biologically compatible polymer which forms a hydrogel when exposed to blood and where the material may not include an active agent such as thrombin. A spring-loaded delivery device as described herein may be used to apply the dried material.

12 Claims, 15 Drawing Sheets

(51) Int. Cl.
*A61M 5/20* (2006.01)
*A61M 5/31* (2006.01)
*A61L 26/00* (2006.01)

(52) U.S. Cl.
CPC ......... *A61L 26/009* (2013.01); *A61L 26/0023* (2013.01); *A61L 26/0033* (2013.01); *A61L 26/0042* (2013.01); *A61L 26/0047* (2013.01); *A61M 35/003* (2013.01); *A61B 2017/00495* (2013.01); *A61B 2017/00893* (2013.01); *A61B 2017/00898* (2013.01); *A61B 2017/00942* (2013.01); *A61L 2400/04* (2013.01); *A61M 5/2033* (2013.01); *A61M 2005/3142* (2013.01)

(58) Field of Classification Search
CPC .............. A61M 5/3148; A61M 5/3137; A61M 2005/2073; A61M 2005/2026; A61M 2005/2086; A61M 2005/202; A61M 2005/2418; A61M 35/003; A61M 5/31501; A61M 5/31505; A61M 2005/206; A61B 17/00491; A61C 1/087; B05C 17/00553; B05C 17/00559; B65D 81/325

See application file for complete search history.

(56) References Cited

U.S. PATENT DOCUMENTS

| | | | |
|---|---|---|---|
| 4,333,457 A | | 6/1982 | Margulies |
| 4,664,128 A | | 5/1987 | Lee |
| 5,167,641 A | | 12/1992 | Schmitz |
| 5,395,345 A | | 3/1995 | Gross |
| 5,882,342 A | * | 3/1999 | Cooper ............... A61M 5/3234 604/110 |
| 6,045,570 A | | 4/2000 | Epstein et al. |
| 6,060,461 A | | 5/2000 | Drake |
| 6,063,061 A | | 5/2000 | Wallace et al. |
| 6,066,325 A | | 5/2000 | Wallace et al. |
| 6,427,878 B1 | | 8/2002 | Greiner-Perth et al. |
| 6,475,193 B1 | * | 11/2002 | Park ...................... A61M 5/204 606/116 |
| 6,706,690 B2 | | 3/2004 | Reich et al. |
| 6,955,682 B2 | | 10/2005 | Luthra et al. |
| 6,992,233 B2 | | 1/2006 | Drake et al. |
| 7,435,425 B2 | | 10/2008 | Qian et al. |
| 7,547,446 B2 | | 6/2009 | Qian et al. |
| 7,871,637 B2 | | 1/2011 | Qian et al. |
| 7,883,693 B2 | | 2/2011 | Sehl et al. |
| 7,923,031 B2 | | 4/2011 | Moller |
| 7,923,431 B2 | | 4/2011 | Wolff |
| 8,076,294 B2 | | 12/2011 | Kinney et al. |
| 8,092,820 B2 | | 1/2012 | Qian et al. |
| 8,119,160 B2 | | 2/2012 | Looney et al. |
| 8,187,625 B2 | | 5/2012 | Greff |
| 8,197,443 B2 | | 6/2012 | Sundar et al. |
| 8,303,981 B2 | | 11/2012 | Wallace et al. |
| 8,357,378 B2 | | 1/2013 | Wallace et al. |
| 8,491,628 B2 | | 7/2013 | Zhu et al. |
| 8,512,729 B2 | | 8/2013 | Wallace et al. |
| 8,575,132 B2 | | 11/2013 | Ji et al. |
| 8,603,511 B2 | | 12/2013 | Wallace et al. |
| 8,642,831 B2 | | 2/2014 | Larsen et al. |
| 8,696,553 B2 | | 4/2014 | Yamane |
| 8,703,176 B2 | | 4/2014 | Zhu et al. |
| 8,815,832 B2 | | 8/2014 | Wang et al. |
| 8,940,335 B2 | | 1/2015 | Goessl |
| 8,961,544 B2 | | 2/2015 | Komlos et al. |
| 9,084,728 B2 | | 7/2015 | Goessl et al. |
| 9,265,858 B2 | | 2/2016 | Larsen |
| 9,295,751 B2 | | 3/2016 | Gaissmaier |
| 9,333,301 B2 | | 5/2016 | Alheidt et al. |
| 9,408,945 B2 | | 8/2016 | Goessl et al. |
| 9,579,671 B2 | | 2/2017 | Decock et al. |
| 9,629,798 B2 | | 4/2017 | Senderoff et al. |
| 2004/0138611 A1 | * | 7/2004 | Griffiths .............. A61M 5/2066 604/82 |
| 2007/0185440 A1 | | 8/2007 | Matsumto et al. |
| 2009/0177156 A1 | * | 7/2009 | MacLean ............ A61M 5/3148 604/189 |
| 2013/0048670 A1 | | 2/2013 | Greter |
| 2014/0114210 A1 | | 4/2014 | Zinnanti |
| 2014/0288529 A1 | * | 9/2014 | Baker ............... A61M 5/31566 434/262 |
| 2015/0282914 A1 | | 10/2015 | Gray |
| 2016/0074602 A1 | | 3/2016 | Wang et al. |
| 2016/0121017 A1 | | 5/2016 | Falus |
| 2016/0375202 A1 | * | 12/2016 | Goodman ............ A61M 11/007 604/500 |

FOREIGN PATENT DOCUMENTS

| | | |
|---|---|---|
| CN | 1921896 | 2/2007 |
| CN | 201346338 | 11/2009 |
| EP | 2289569 B1 | 3/2011 |
| EP | 2358409 B1 | 8/2011 |
| JP | 2001-521417 | 11/2001 |
| JP | 2003-501215 | 1/2003 |
| WO | 03055531 | 7/2003 |
| WO | 2008062908 | 5/2008 |
| WO | 2009123903 | 10/2009 |
| WO | 2011144916 | 11/2011 |
| WO | WO-2011143785 A1 * | 11/2011 ....... B05C 17/00586 |
| WO | WO-2012022810 A2 * | 2/2012 .......... A61M 5/2033 |
| WO | WO-2015022295 A2 * | 2/2015 .............. A61M 5/24 |
| WO | 2015076252 A1 | 5/2015 |
| WO | WO-2015117135 A1 * | 8/2015 ........ A61M 5/31501 |
| WO | 2016039969 | 3/2016 |
| WO | 2016209442 | 12/2016 |
| WO | WO-2017210421 A1 * | 12/2017 ....... A61B 17/00491 |
| WO | WO-2019086371 A1 * | 5/2019 .......... A61M 5/2033 |

OTHER PUBLICATIONS

International Search Report and Written Opinion issued in International Patent Application No. PCT/US2018/058500 dated Apr. 17, 2019.
Instructions for Use for Ethicon SURGIFLO Hemostatic Matrix Kit with Thrombin. Released Jul. 24, 2017. 16 pages.
Instructions for Use for Baxter FLOSEAL Hemostatic Matrix, 5 mL. Rev. Date: Jun. 1, 2016. 2 pages.
China Office Action dated Dec. 13, 2021 for App. No. 201880070371.3 (11 pages).
India Office Action dated Jun. 1, 2021 for App. No. 202017017876 (6 pages).
India Office Action dated Mar. 23, 2022 for App. No. 202118055685 (5 pages).
Japan Office Action dated Jun. 28, 2022 for App. No. 2020-517467 (7 pages).
China Office Action dated Jul. 5, 2022 for App. No. 201880070371.3 (4 pages).

* cited by examiner

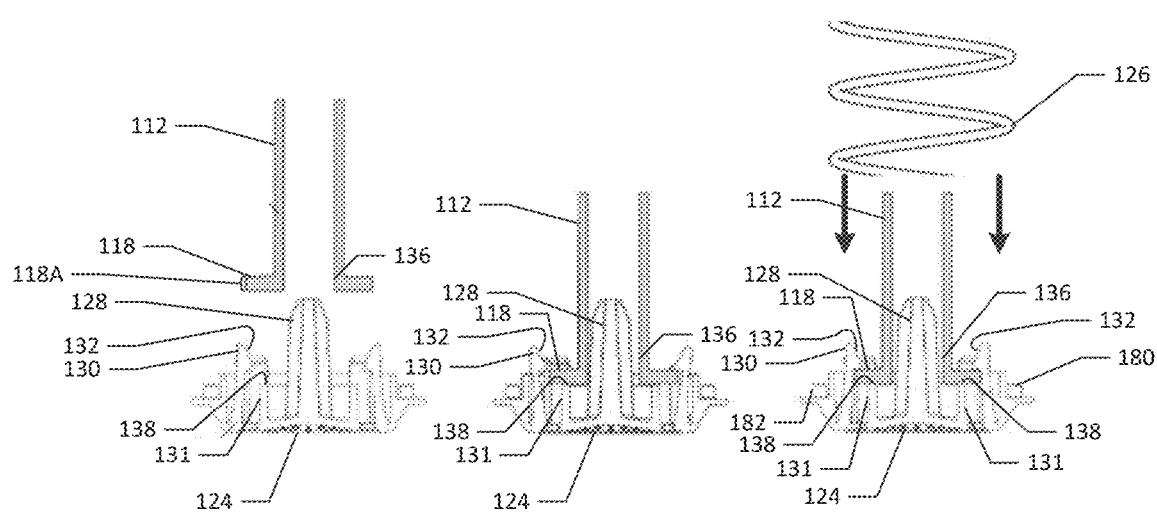

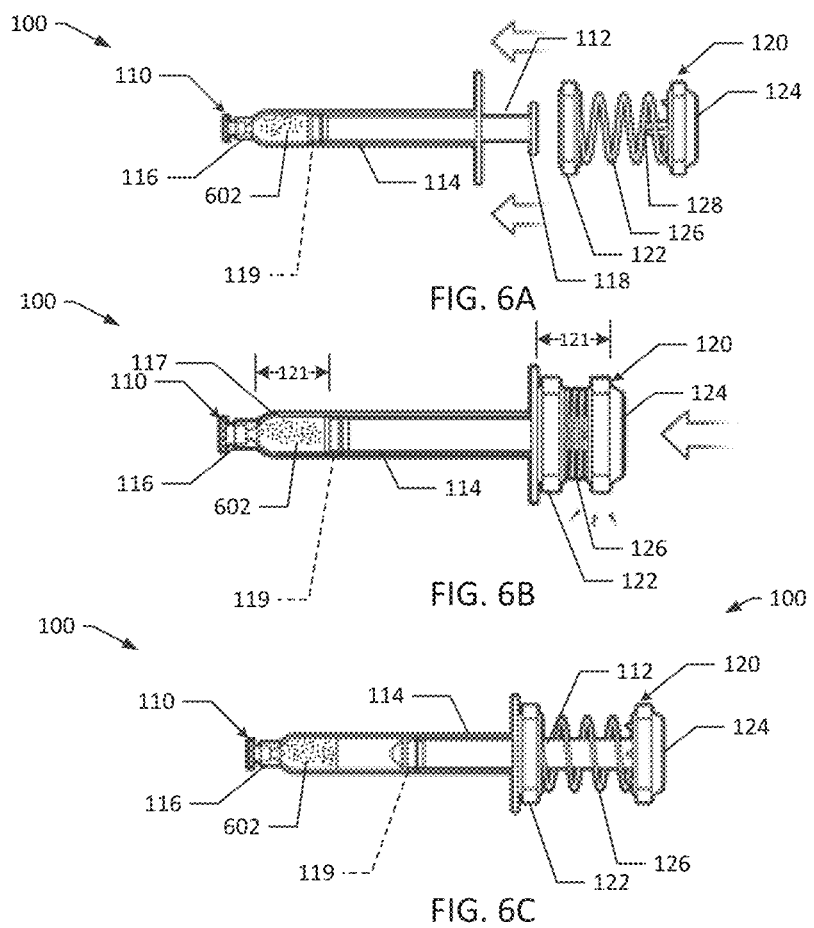

POLYMERIC COMPOSITIONS, DELIVERY DEVICES, AND METHODS

PRIORITY CLAIM

This application claims priority to U.S. Provisional Application No. 62/542,615, entitled "Dry Gelatin Hemostatic Agent," filed Aug. 8, 2017, and U.S. Provisional Application No. 62/581,453, entitled "Polymeric Compositions, Delivery Devices, and Methods," filed Nov. 3, 2017, the entire respective contents of which are incorporated herein by reference and relied upon.

BACKGROUND

Preventing excessive bleeding is important in many medical applications. Numerous procedures and materials have been proposed to prevent excessive bleeding and reduce transfusion rates and minor complications in surgery, including cardiovascular surgery. Such procedures include introducing barrier materials such as metals, polymers, and natural materials onto a bleeding site. These products, however, may not conform well to the underlying tissue. Other materials that have been implemented include nylon, cellophane, polytetrafluoroethylene, polyethylene, siloxane, elastomers, and polylactic acid copolymer films. Unfortunately, many of these materials are not biodegradable and, therefore, remain in the body with unpredictable and potentially undesirable consequences.

Additionally, it is often difficult to place and immobilize implants properly onto the bleeding site. Using non-solid anti-adhesive materials may also be problematic, because such materials often should be sufficiently fluid to enter and conform to the regions being treated, while simultaneously being sufficiently viscous enough to remain on the bleeding site until the tissue is healed. These objectives also have to be balanced with the requirements of biocompatibility and resorbability.

Certain compositions currently used to prevent excessive bleeding implement an aqueous carrier. For example, compositions may be delivered in the form of a powder, which is biocompatible and may permit optimization of the release characteristics, including release rate, composition persistence, drug carrying capacity, product delivery characteristics (such as injectability), and the like. However, initial preparation of an aqueous carrier or hydrogel composition requires additional steps, which may be undesirable in certain environments such as emergency medicine situations. Moreover, the aqueous carriers may require active agents, such as thrombin, which require unwanted additional preparation and delivery steps.

Bleeding prevention compositions are delivered to the bleeding site, on or in the body, necessitating a high degree of user-control. The compositions are delivered in a controlled fashion, so as to target the site of therapeutic effect, e.g., the bleeding site. Compositions may vary in physical characteristics. For example, viscous compositions may require a different delivery device than solid compositions. The type of composition delivered, therefore, dictates its delivery device and mode of delivery.

For the above reasons, it is desirable to provide improved polymeric compositions and related methods for preventing excessive bleeding following surgery and other trauma. Similarly, it is desirable to provide delivery devices, delivery systems, and related methods, for precise administration of polymeric compositions. Improved polymeric compositions, delivery devices, and methods are needed accordingly.

SUMMARY

To improve medical treatment, especially to prevent excessive bleeding, new polymeric compositions, delivery devices, delivery systems, and methods of delivery are described herein. The present disclosure seeks to implement new polymeric compositions that eliminate undesirable features of current compositions, such as viscosity of the material, aqueous carrier requirements, active agent requirements, etc. The present disclosure sets forth methods for inhibiting bleeding by applying a powdered material topically to a wound site in one embodiment. The powdered material does not require an aqueous carrier, or an active agent, such as thrombin. The present disclosure also sets forth devices and methods for delivering the new polymeric compositions to the patient with a high degree of user control, regarding both the delivery location and the delivery rate. The present disclosure further provides for new devices, systems, and methods for delivering powdered material topically to a wound site.

In light of the disclosure herein, and without limiting the scope of the invention in any way, in a first aspect of the present disclosure, which may be combined with any other aspect listed herein unless specified otherwise, a method for inhibiting bleeding includes applying a powdered or dried material topically to a wound site. The material includes a biologically compatible polymer (which may be cross-linked or non-crosslinked, or have both cross-linked and non-cross-linked components), which forms a hydrogel when exposed to blood, and does not comprise an active agent.

In a second aspect of the present disclosure, which may be combined with any other aspect listed herein unless specified otherwise, the hydrogel comprises dry, cross-linked gelatin polymer particles. Alternatively the hydrogel may comprise dry, non-cross-linked gelatin polymer particles.

In a third aspect of the present disclosure, which may be combined with any other aspect listed herein unless specified otherwise, the biologically compatible polymer remains in the body for a substantial period of time that corresponds to time for wound healing and can be expected to degrade fully as the wound is healed. For example, the degradation time may be a month or less, or 15 to 30 days, or 6 weeks to 8 weeks, or may be two months or more.

In a fourth aspect of the present disclosure, which may be combined with any other aspect listed herein unless specified otherwise, the biologically compatible polymer is sized and dimensioned such that the polymer forms the hydrogel with a sub-unit or particle size in the range from 0.01 mm to 1 mm; or more specifically, from 0.01 mm to 0.1 mm. For example, the biologically compatible polymer may form a mat made of smaller pieces such that the polymer dissolves in solution. The sub-units or particles may be irregularly shaped.

In a fifth aspect of the present disclosure, which may be combined with any other aspect listed herein unless specified otherwise, the biologically compatible polymer has an equilibrium swell in the range from 30% to 1000% by weight.

In a sixth aspect of the present disclosure, which may be combined with any other aspect listed herein unless specified otherwise, the biologically compatible polymer is present at from 50 percent by weight to 100 percent by weight of the material, or from 80% to 90% by weight of the material.

In a seventh aspect of the present disclosure, which may be combined with any other aspect listed herein unless specified otherwise, the material further comprises an additive present at from 1 percent by weight to 20 percent by weight of the material, or from 5% to 15% by weight of the material. For example, 100 to 1000 milligrams of the additive may be used, preferably 500 to 1050 milligrams, depending on the additive. The additive may be polyvinylpyrrolidone, dextran, polyethylene glycol or similar agents. These additives may be removed from the final product through irrigation or other similar means, or the biologically compatible product may be produced without any additives.

In an eighth aspect of the present disclosure, which may be combined with any other aspect listed herein unless specified otherwise, the additive is selected from the group consisting of polyethylene glycol, dextran, polyvinylpyrrolidone, or other large weight polymers, sorbitol, and glycerol and combinations thereof, preferably polyethylene glycol, dextran, and/or polyvinylpyrrolidone.

In a ninth aspect of the present disclosure, which may be combined with any other aspect listed herein unless specified otherwise, the biologically compatible polymer is a cross-linked protein selected from the group consisting of gelatins, collagens, albumin, hemoglobin, fibrinogen, fibroin, fibronectin, elastin, keratin, laminin, casein, and sections thereof, such as fibronectin regions or collagen fragments, as well as mixtures of any two or more of the foregoing, preferably gelatin. The biologically compatible polymer may be fully cross-linked, partially cross-linked or not cross-linked.

In a tenth aspect of the present disclosure, which may be combined with any other aspect listed herein unless specified otherwise, the biologically compatible polymer is a cross-linked carbohydrate or carbohydrate derivative selected from the group consisting of glycosaminoglycans, including, heparin, heparin sulfate, hyaluronic acid, chondroitin sulfate, keratin sulfate, and/or other extracellular matrix proteins, starches, celluloses, hemicelluloses, xylan, agarose, alginate, and chitosan.

In an eleventh aspect of the present disclosure, which may be combined with any other aspect listed herein unless specified otherwise, the biologically compatible polymer is a cross-linked, non-biologic hydrogel-forming polymer or copolymer selected from the group consisting of polyacrylates, polymethacrylates, polyacrylamides, polyvinyl alcohol polymers, polylactides-glycolides, polycaprolactones, polyoxyethylenes, polyethylene glycol, and copolymers thereof.

In a twelfth aspect of the present disclosure, which may be combined with any other aspect listed herein unless specified otherwise, the material further includes a non-cross-linked biologically compatible polymer, the polymer comprising a protein selected from the group consisting of gelatin, collagen, albumin, elastin, and keratin, preferably gelatin.

In a thirteenth aspect of the present disclosure, which may be combined with any other aspect listed herein unless specified otherwise, the material further includes a non-cross-linked biologically compatible polymer, the polymer comprising a carbohydrate or carbohydrate derivative selected from the group consisting of glycosaminoglycans, alginate, starch, cellulose, and derivatives thereof.

In a fourteenth aspect of the present disclosure, which may be combined with any other aspect listed herein unless specified otherwise, the material is in the form of gelatin granules and swells by about 30% to about 80% in diameter upon contact with blood.

In a fifteenth aspect of the present disclosure, which may be combined with any other aspect listed herein unless specified otherwise, the active agent not present in the material is selected from the group consisting of antibiotics, anti-neoplastic agents, bacteriostatic agents, bactericidal agents, antiviral agents, anesthetics, anti-inflammatory agents, hormones, anti-angiogenic agents, antibodies, enzymes, enzyme inhibitors, and neurotransmitters.

In a sixteenth aspect of the present disclosure, which may be combined with any other aspect listed herein unless specified otherwise, the active agent not present in the material is an additional hemostatic substance.

In a seventeenth aspect of the present disclosure, which may be combined with any other aspect listed herein unless specified otherwise, the active agent not present in the material is a clotting factor.

In an eighteenth aspect of the present disclosure, which may be combined with any other aspect listed herein unless specified otherwise, the active agent not present in the material is thrombin.

In a nineteenth aspect of the present disclosure, which may be combined with any other aspect listed herein unless specified otherwise, a delivery device includes a retainer ring, a cap, and a spring, disposed between the retainer ring and the cap, the retainer ring and the cap structured to capture opposing ends of the spring such that the spring is retained by the retainer ring and the cap and the cap, spring, and retainer ring form an integral assembly.

In a twentieth aspect of the present disclosure, which may be combined with any other aspect listed herein unless specified otherwise, the cap includes a plurality of dependent engagement structures positioned to lockingly engage a plunger of a syringe.

In a twenty-first aspect of the present disclosure, which may be combined with any other aspect listed herein unless specified otherwise, the plurality of dependent engagement structures includes a post, configured to extend into and engage the plunger of the syringe, wherein the post is formed integrally with the cap.

In a twenty-second aspect of the present disclosure, which may be combined with any other aspect listed herein unless specified otherwise, the post extends along an axis of the spring towards the retainer ring and is disposed concentrically within the spring.

In a twenty-third aspect of the present disclosure, which may be combined with any other aspect listed herein unless specified otherwise, the plurality of dependent engagement structures includes a plurality of latch arms, the plurality of latch arms formed integrally with the cap and adapted to lockingly engage a plunger of a syringe.

In a twenty-fourth aspect of the present disclosure, which may be combined with any other aspect listed herein unless specified otherwise, the plurality of latch arms extend from an inner surface of the cap, wherein an end of each of the plurality of latch arms includes an angled cam surface and a latching shoulder, the latching shoulder defining a latch surface opposing the inner surface of the cap, wherein the cap further includes a raised step surface projecting from the inner surface of the cap for cooperatively locking a flanged end of the plunger between the latch surface and the raised step surface.

In a twenty-fifth aspect of the present disclosure, which may be combined with any other aspect listed herein unless specified otherwise, the cap includes a plurality of inwardly extending clips sited and arranged to capture one of the opposing ends of the spring.

In a twenty-sixth aspect of the present disclosure, which may be combined with any other aspect listed herein unless specified otherwise, the retainer ring includes a plurality of inwardly extending clips sited and arranged to capture one of the opposing ends of the spring.

In a twenty-seventh aspect of the present disclosure, which may be combined with any other aspect listed herein unless specified otherwise, the spring is a compression spring, such that the spring biases the cap away from the retainer ring.

In a twenty-eighth aspect of the present disclosure, which may be combined with any other aspect listed herein unless specified otherwise, the spring has a spring constant in the range of 1 to 10 pound-force.

In a twenty-ninth aspect of the present disclosure, which may be combined with any other aspect listed herein unless specified otherwise, a delivery system includes a syringe, a powdered substance to be delivered, and a delivery device. The syringe includes a plunger and a barrel, the plunger configured to engage and translate along an inner surface of the barrel. The powdered substance is disposed within the barrel of the syringe. The delivery device includes a retainer ring, a cap, and a spring, disposed between the retainer ring and the cap, the retainer ring and the cap structured to capture opposing ends of the spring such that the spring is retained by the retainer ring and the cap. The cap includes a post, the post configured to extend into and engage the plunger of the syringe. The cap includes a plurality of latch arms, configured to extend from an inner surface of the cap, wherein an end of each of the plurality of latch arms includes an angled cam surface and a latching shoulder, the latching shoulder defining a latch surface opposing the inner surface of the cap, wherein the cap further includes a raised step surface projecting from the inner surface of the cap for cooperatively locking a flanged end of the plunger between the latch surface and the raised step surface. The delivery device is moveable between a compressed position and a relaxed position. In the compressed position, the cap is moved towards the retainer ring and the spring is compressed, thereby translating the plunger towards a distal end of the syringe. In the relaxed position, the cap is moved away from the retainer ring and the spring is relaxed, thereby translating the plunger toward a proximal end of the syringe.

In a thirtieth aspect of the present disclosure, which may be combined with any other aspect listed herein unless specified otherwise, the syringe barrel defines an orifice, discharge opening, or aperture at a distal end of the barrel, wherein the syringe is configured to expel a material from the orifice.

In a thirty-first aspect of the present disclosure, which may be combined with any other aspect listed herein unless specified otherwise, the material expelled is a biologically compatible polymer which forms a hydrogel when exposed to blood.

In a thirty-second aspect of the present disclosure, which may be combined with any other aspect listed herein unless specified otherwise, the barrel retains a first material adjacent to a second material.

In a thirty-third aspect of the present disclosure, which may be combined with any other aspect listed herein unless specified otherwise, the post extends along an axis of the spring towards the retainer ring and is disposed concentrically within the spring.

In a thirty-fourth aspect of the present disclosure, which may be combined with any other aspect listed herein unless specified otherwise, a proximal end of the plunger defines a receptacle sited and arranged to receive and engage the post.

In a thirty-fifth aspect of the present disclosure, which may be combined with any other aspect listed herein unless specified otherwise, the spring is a compression spring, such that the spring biases the cap away from the retainer ring.

In a thirty-sixth aspect of the present disclosure, which may be combined with any other aspect listed herein unless specified otherwise, the retainer ring and the cap each include a plurality of inwardly extending clips sited and arranged to capture one of the opposing ends of the spring.

In a thirty-seventh aspect of the present disclosure, which may be combined with any other aspect listed herein unless specified otherwise, a method of enabling use of a delivery device includes enabling the coupling of a cap of a delivery device to a plunger of a syringe, including inserting a post of the cap into a proximal end of the plunger. The method includes enabling the depressing of the cap of the delivery device, wherein, responsive to depressing the cap, a spring of the delivery device compresses, and the plunger translates towards a distal end of the syringe. The method includes enabling the releasing of the cap of the delivery device, wherein, responsive to releasing the cap, the spring of the delivery device expands, and the plunger translates towards a proximal end of the syringe. The method includes enabling the repeating of the depressing and releasing of the cap to sequentially and intermittently expel a desired amount of a material from the distal end of the syringe with each compression stroke.

In a thirty-eighth aspect of the present disclosure, which may be combined with any other aspect listed herein unless specified otherwise, the material is a dry material.

In a thirty-ninth aspect of the present disclosure, which may be combined with any other aspect listed herein unless specified otherwise, a dry powder hemostat includes dry particles of cross-linked bovine gelatin and non-crosslinked bovine gelatin. The dry particles may be sized from 250 µm to 500 µm, or between 325 and 450 µm, or between 300 and 400 µm. The particles are denser than other particles used for hemostasis. The dry powder hemostat is substantially free of added thrombin. The dry powder hemostat, when added directly to the site of a bleeding wound absorbs blood and wound exudate fluids, remains at the bottom of the wound without floating of the particles and exhibits a 70% swell from a dry state, and promotes hemostasis.

In a fortieth aspect of the present disclosure, which may be combined with any other aspect listed herein unless specified otherwise, a kit includes a pre-filled syringe, including dry particles of cross-linked bovine gelatin and non-crosslinked bovine gelatin and a delivery device. The delivery device includes a retainer ring, a cap, and a spring, disposed between the retainer ring and the cap. The delivery device is configured to be coupled to the pre-filled syringe. Responsive to depressing the cap, a spring of the delivery device compresses, the plunger translates towards a distal end of the pre-filled syringe, and dry particles of cross-linked bovine gelatin and non-crosslinked bovine gelatin are expelled from the distal end of the pre-filled syringe. Responsive to releasing the cap, the spring of the delivery device expands, and the plunger translates towards a proximal end of the pre-filled syringe.

In a forty-first aspect, which may be combined with any other aspect listed herein unless specified otherwise, the system may be modified to increase the quantity of powder or material expressed with each depression of the plunger. Depending upon the medical application, the system may include a modified orifice that allows a relatively larger quantity of material or powder to exit the pre-filled syringe when the syringe plunger is depressed. The system may also achieve an increase in the quantity of powder or material expressed with each depression of the plunger by increasing the length of the plunger.

In a forty-second aspect, which may be combined with any other aspect listed herein unless specified otherwise, the system may be modified to decrease the quantity of powder or material expressed with each depression of the plunger. Depending upon the medical application, the system may include a modified orifice that allows a relatively smaller quantity of material or powder to exit the pre-filled syringe when the syringe plunger is depressed. The system may also achieve a decrease in the quantity of powder or material expressed with each depression of the plunger by decreasing the length of the plunger. The system may also achieve a decrease in the quantity of powder or material expressed with each depression of the plunger by including operably coupling the syringe to a check valve.

In a forty-third aspect, any of the structure, functionality, and alternatives discussed in connection with any of FIGS. 1 to 15 may be combined with the structure, functionality, and alternatives discussed in connection with any other FIGS. 1 to 15.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

Understanding that the figures depict only typical embodiments of the invention and are not to be considered to be limiting the scope of the present disclosure, the present disclosure is described and explained with additional specificity and detail through the use of the accompanying figures. The figures are listed below.

FIGS. 5A to 5C are side views of a cap and a syringe plunger, according to example embodiments of the present disclosure.

FIGS. 6A to 6C are side views of a delivery device and a syringe, according to an example embodiment of the present disclosure.

DETAILED DESCRIPTION OF EXAMPLE EMBODIMENTS

Figure 1:
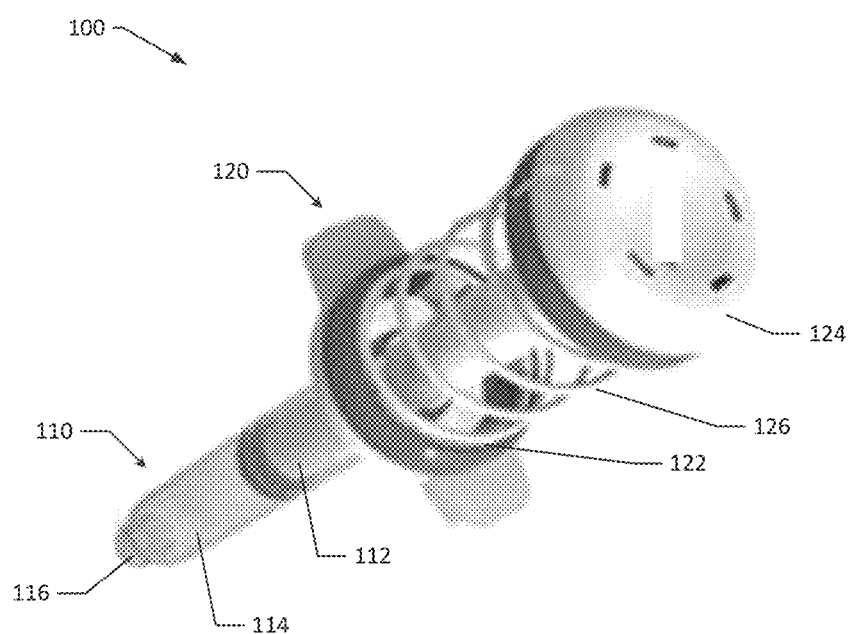
FIG. 1 is perspective view of a delivery system, including a delivery device and a syringe, according to an example embodiment of the present disclosure.

As discussed briefly above, this disclosure is, in various embodiments, directed to systems, methods, and devices for inhibiting bleeding by applying a powdered material topically to a wound site and to such powdered material itself. The powdered material, which does not comprise an active agent such as thrombin, is an effective ready-to-use powder hemostat. Similarly, this disclosure is directed to delivery devices, delivery systems, and related methods for precise administration of polymeric compositions, such as a powder hemostat.

Polymeric Composition

The materials disclosed herein may comprise cross-linked or non-cross-linked biologically compatible polymers which are relatively persistent, usually having a degradation time comparable to the time for wound healing, for example, in the range from 10 days to 120 days. By comparison, non-cross-linked biologically compatible polymer of the present disclosure is fragmented, i.e., is present in the materials as discrete dry particles, so that upon hydration (e.g., in blood), the polymer will form a hydrogel with a sub-unit size in a range from 0.01 mm to 5 mm, for example, from 0.05 mm to 1 mm. In some cases, the biologically compatible polymer is swellable, and has an equilibrium swell that when fully hydrated is in the range from 200% to 5,000%, for example, in the range from 400% to 5,000% and/or from 500% to 1000%.

Equilibrium swell, expressed as a percentage, may be defined as the ratio of the difference between the equilibrium wet weight and dry weight of the cross-linked polymer and the dry weight of the polymer as follows:

$$\text{Equilibrium Swell (\%)} = \frac{\text{Wet Weight} - \text{Dry Weight}}{\text{Dry Weight}} \times 100$$

The equilibrium wet weight may be measured after the polymer has had an extended period of time in contact with the wetting agent, after which the polymer can no longer take-up or absorb significant additional wetting agent. For example, a cross-linked polymer that takes-up or absorbs five times its dry weight in water at equilibrium may be said to have an equilibrium swell of 500% in water. A cross-linked polymer that takes-up or absorbs no water (that is, its equilibrium wet weight is the same as its dry weight) may be said to have an equilibrium swell of 0% in water.

The cross-linked polymer may be the predominant component of the material, typically being present at from 50 weight % to 100 weight % of the total weight of the material, for example, from 80 weight % to 100 weight %, from 50 weight % to 95 weight %, and/or from 80 weight % to 95 weight % of the total weight of the material. An optional non-cross-linked material, if present, may form a much smaller portion of the material, be present typically at from 50 weight % to 1 weight % of the total weight of material, for example, from 20 weight % to 1 weight %. Optionally, an additive is included in the material, being present, for example, from 1 weight % to 20 weight % of the total weight of the material, for example, from 3 weight % to 15 weight % of the material. For example, 100 to 1000 milligrams of the additive may be used, preferably 500 to 1050 milligrams, depending on the additive.

Suitable additives may be polyvinylpyrrolidone, dextran, other large weight polymers, polyethylene glycol or similar agents or combinations thereof. These additives may be removed from the final product through irrigation or other similar means, or the biologically compatible product may be produced without any additives.

The polymer which is cross-linked may be a protein, carbohydrate or carbohydrate derivative, non-biologic hydrogel-forming polymer or copolymer, or other biologically compatible polymer or combination of polymers which can form a hydrogel. Suitable polymers include, but are not limited to, proteins, such as gelatins, collagens, albumin, hemoglobin, fibronectin, fibrinogen, fibroin, elastin, keratin, laminin, casein, and the like, including sections thereof, such as fibronectin regions or collagen fragments. Suitable carbohydrate and carbohydrate derivative polymers include, but are not limited to, glycosaminoglycans, including, heparin, heparin sulfate, hyaluronic acid, chondroitin sulfate, keratin sulfate, and/or other extracellular matrix proteins, starches, celluloses, hemicelluloses, xylan, agarose, alginate, chitosan, and the like. Exemplary non-biologic hydrogel-forming polymers and copolymers include, but are not limited to, polyacrylates, polymethacrylates, polyacrylamides, polyvinyl polymers, polylactides-glycolides, polycaprolactones, polyoxyethylenes, polyethylene glycol, and copolymers thereof. The degree of cross-linking of the cross-linked polymer may be selected to provide a desired swellability within the range set forth above. Surface changes may further induce coagulation.

In some cases, the biologically compatible polymer is a cross-linked non-biologic hydrogel-forming polymer or copolymer selected from the group consisting of polyacrylates, polymethacrylates, polyacrylamides, polyvinyl polymers, polylactides-glycolides, polycaprolactones, polyoxyethylenes, and copolymers thereof.

In some cases, the cross-linked polymer is dispersed in a dried matrix of the optional non-cross-linked polymer. The optional non-cross-linked biologically compatible polymer may be a protein or a carbohydrate (or carbohydrate derivative) and may be the same polymer as the polymer which is cross-linked. Exemplary proteins include, but are not limited to, gelatin, collagen, albumin, elastin, keratin, and the like. Exemplary carbohydrates and carbohydrate derivatives include, but are not limited to, glycosaminoglycans, alginate, starch, cellulose, derivatives thereof, and the like. The non-cross-linked polymer may also be non-biological water soluble polymer, such as any of the hydrogel-forming polymers and co-polymers set forth above. An exemplary hemoactive material according to the present disclosure comprises a dry matrix of non-cross-linked gelatin polymer or a dry cross-linked gelatin polymer present as particles dispersed in the dry gelatin matrix.

The materials disclosed herein may be formed as sheets, powders, pellets, plugs, tubes, split tubes, cylinders, irregular granules or particles, or the like. These may be provided without compaction in a loose powder with interstices. Such forms of the material may be produced sterilely (e.g., by aseptic processing) or sterilized and provided in sterile packs as part of kits. Sterilization may occur via electronic-beam, γ-irradiation, or via ethylene oxide or other chemical sterilant, or the like. In addition to the sterile packs containing the solid forms of the materials, the kits may also contain instructions for use setting forth methods for inhibiting bleeding by placing the sterilized materials at a target site in tissue (e.g., a wound or other site of bleeding tissue) with a delivery device or delivery system, such as those disclosed herein.

As a further aspect of the present disclosure, hemoactive materials may be made by suspending particles of cross-linked biologically compatible polymer as described above in an aqueous medium. The aqueous medium is then dried to form a solid phase comprising the dried polymeric particles. Lyophilization (freeze-drying) is one drying technique. Air drying, heat-assisted drying, spray drying, fluid-bed drying, molding, and other methods could also be used under certain circumstances.

In some cases, the material is in the form of gelatin granules and swells in diameter by about 30% to about 80% upon contact with blood, for example, about 40% to about 80%, about 50% to about 80%, about 60% to about 80%, about 30% to about 70%, about 40% to about 70%, about 50% to about 70%, about 60% to about 70%, and/or about 70%.

The biologically compatible polymer is sized and dimensioned such that the polymer forms the hydrogel with a sub-unit or particle size in the range from 0.01 mm to 1 mm; or more specifically, from 0.01 mm to 0.1 mm.

In some cases, the active agent is selected from the group consisting of antibiotics, anti-neoplastic agents, bacteriostatic agents, bactericidal agents, antiviral agents, anesthetics, anti-inflammatory agents, hormones, anti-angiogenic agents, antibodies, enzymes, enzyme inhibitors, and neurotransmitters. In some cases, the active agent is a hemostatic substance. In some cases, the active agent is a clotting factor. In some cases, the active agent is thrombin.

Compositions according to the present disclosure may comprise dried hemostatic materials, including a biologically compatible polymer that may be cross-linked. The term "biologically compatible" may mean that the materials will meet the criteria in standard #ISO 10993-1 (International Organization for Standardization, Geneva, Switzerland). Generally, biologically compatible materials are free from pyrogenic substances and will not cause adverse biological effects when applied to human tissue. The compositions of the present disclosure may be resorbable. The term "resorbable" may mean that the compositions will degrade or solubilize when placed directly onto or into a target site in a patient's body over a time period of less than one year, usually from 1 day to 120 days. If present, the non-cross-linked polymer components of the materials of the present disclosure may typically degrade or solubilize much more quickly, typically in several minutes or less. The remaining cross-linked polymer may form a hydrogel at the placement site, where the hydrogel will persist over time, but will be resorbable as just set forth.

Suitable cross-linked polymers according to the present disclosure are described in detail in U.S. Pat. No. 6,066,325, the full disclosure of which is incorporated herein by reference and relied upon. The biologically compatible polymers may be molecular cross-linked. The term "molecular cross-linked," may mean that the materials comprise polymer molecules (i.e., individual chains) which are attached by bridges composed of either an element, a group, or a compound, where the backbone atoms of the polymer molecules are joined by chemical bonds. Alternatively, the cross-linked polymers may be formed by non-covalent interactions such as electrostatic, ionic or hydrophobic. Cross-linking may be effected in a variety of ways, as will be described in greater detail below.

The term by "hydrogel," may mean that the composition comprises a hydrophilic cross-linked biologic or non-biologic polymer, as defined in more detail below, which absorbs a large quantity of water or an aqueous buffer. The hydrogels have little or no free water, i.e., water cannot be removed from the hydrogel by simple filtration.

The term "percent swell," means that the dry weight is subtracted from the wet weight, divided by the dry weight and multiplied by 100, where wet weight is measured after the wetting agent has been removed as completely as possible from the exterior of the material, e.g., by filtration, and where dry weight is measured after exposure to an elevated temperature for a time sufficient to evaporate the wetting agent, e.g., 2 hours at 120° C.

The term "equilibrium swell" may be defined as the percent swell at equilibrium after the polymeric material has been immersed in a wetting agent for a time period sufficient for water content to become constant, typically 18 to 24 hours.

The term "target site" may be the location to which the hemostatic material is to be delivered for therapeutic effect, e.g. the bleeding site. Usually, the target site will be the tissue location of interest. In some cases, however, the hemostatic material may be administered or dispensed to a location near the location of interest, e.g., when the material swells in situ to cover the location of interest.

The biologically compatible polymers of the present disclosure may be formed from biologic and non-biologic polymers. Suitable polymers are described, for example, in U.S. Pat. Nos. 6,063,061, 6,066,325, 6,706,690, 7,435,425, 7,547,446, 8,092,820, 8,303,981, 8,357,378, 8,512,729, 8,603,511, 8,940,335, 9,084,728, and 9,408,945, the full disclosures of which are incorporated herein by reference and relied upon. Suitable biologic polymers include proteins, such as gelatin, soluble collagen, albumin, hemoglobin, casein, fibronectin, elastin, keratin, laminin, and derivatives and combinations thereof. One preferred use is the use of gelatin or soluble non-fibrillar collagen, more preferably gelatin, and exemplary gelatin formulations are set forth below. Other suitable biologic polymers include polysaccharides, such as glycosaminoglycans (e.g., hyaluronic acid and chondroitin sulfate), starch derivatives, xylan, cellulose derivatives, hemicellulose derivatives, agarose, alginate, chitosan, and derivatives and combinations thereof. Suitable non-biologic polymers will be selected to be degradable by either of two mechanisms, i.e., (1) break down of the polymeric backbone or (2) degradation of side chains which result in aqueous solubility. Exemplary non-biologic hydrogel-forming polymers include synthetics, such as polyacrylates, polymethacrylates, polyacrylamides, polyvinyl resins, polylactides-glycolides, polycaprolactones, polyoxyethylenes, polyethylene glycol, and derivatives and combinations thereof.

The polymer molecules may be cross-linked in any manner suitable to form a hemostatic material according to the present disclosure. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as γ-radiation, to activate the side polymer to permit cross-linking reactions. Alternatively, radical forming agents such as TEMPO, TEMD, halogens, azo-compounds, organic or inorganic peroxides, ATRP may be used, alone or in conjunction with alkene functionalization. Dehydrothermal cross-linking methods are also suitable. Increasing the extent of cross-linking, may be achieved by elevating the holding temperature, extending the duration of the holding time, or a combination of both. Operating under reduced pressure may accelerate the cross-linking reaction. Suitable methods for cross-linking gelatin molecules are described below.

The materials of the present disclosure may include an additive to increase the malleability, flexibility, and rate of hydration of a resulting hydrogel composition in use. In some cases, the additive is present in the non-cross-linked biologically compatible polymer. The additive may be an alcohol, such as polyethylene glycol, sorbitol, or glycerol, and in a preferred embodiment is polyethylene glycol having a molecular weight ranging from about 20 to 2000 D, which may be about 400 D. The additives are present in the compositions during manufacture at from about 0.1% of the solids by weight to 30% of the solids by weight, usually from 1% of the solids by weight to 20% of the solids by weight, 3% of the solids by weight to 15% of the solids by weight, and/or from 1% of the solids by weight to 5% of the solids by weight, of the composition. The additives are particularly beneficial for use with materials having a high solids content, typically above 10% by weight of the composition (without additives). The additives may be fully removed in the final composition. Conveniently, the additive may be added to the suspension of the cross-linked polymer before drying.

Exemplary methods for producing molecular cross-linked gelatins are as follows. Gelatin is obtained (it may be pre-ground to a target size) and placed in an aqueous buffer to form a non-cross-linked hydrogel, typically having a solids content from 1% to 70% by weight, usually from 3% to 10% by weight. The gelatin is cross-linked, typically by exposure to either glutaraldehyde (e.g., 0.01% to 0.5% w/w, for at least overnight and preferably 15-25 hours and ideally 17-21 hours at 0 to 15° C. in an aqueous buffer maintaining the pH at 9-9.5), sodium periodate (e.g., 0.05 M, held at 0 to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of γ or electron beam radiation. Prior to the exposure to the cross-linking agent, the gelatin is prewarmed by heating to 30-35° C. for 15-25 minutes and then cooled below 10-20° C., ideally heated to 35° C. for 20 minutes for compositions including additives, or for 1 hour at 27° C. and then cooled for compositions without additives. Alternatively, gelatin particles may have a solids content of 1% to 70% by weight, usually 3% to 10% by weight, and cross-linked by exposure to a cross-linking agent, typically glutaraldehyde (e.g., 0.01% to 0.5% w/w, overnight at room temperature). In the case of aldehydes, the pH may be held from about 6 to 11, and in one preferred embodiment from 7 to 10. When cross-linking with glutaraldehyde, the cross-links appear to be formed via Schiff bases or via another reaction, which may be stabilized by subsequent reduction, e.g., by treatment with sodium borohydride. After cross-linking, the resulting granules may be washed in water and optionally rinsed in an alcohol and dried. The resulting cross-linked gelatin may then be used as described in more detail hereinafter. Alternatively, the gelatin may be mechanically disrupted prior to or after cross-linking, also as described in more detail hereinafter.

Exemplary methods for producing molecular cross-linked gelatin compositions having equilibrium percent swells in the range from about 30% to about 1000%, preferably about 30% to 80% in diameter, or 400% to about 500%, about 500% to about 1000%, or about 600% to about 950%, are as follows. Gelatin is obtained and placed in an aqueous buffer (typically at a pH of 6 to 11, in one preferred embodiment at a pH between 7 and 10) containing a cross-linking agent in solution (typically glutaraldehyde, preferably at a concentration of 0.01% to 0.5% w/w) to form a hydrogel, typically having a solids content from 1% to 70% by weight, usually from 3% to 10% by weight. The hydrogel is well mixed and held overnight at 0 to 15° C. as cross-linking takes place. It is then rinsed three times with deionized water, optionally rinsed twice with an alcohol (preferably methyl alcohol, ethyl alcohol, or isopropyl alcohol) and allowed to dry at room temperature. Optionally, the hydrogel may be treated with sodium borohydride to further stabilize the cross-linking.

Optional non-cross-linked biologically compatible polymers may be included and may be formed from many of the same polymers described above for the cross-linked components. By using the polymers in a non-cross-linked form, however, the polymers will generally be less persistent in the presence of blood or other aqueous medium and are thus suitable as binders for holding the cross-linked materials of the present disclosure together. Alternatively, additive polymers may be fully removed as part of the manufacturing process. Particularly suitable protein non-cross-linked polymers include gelatins, collagens, elastin, albumin, keratin, and the like. Other suitable non-cross-linked carbohydrate and carbohydrate derivative polymers include glycosaminoglycans, including, heparin, heparin sulfate, hyaluronic acid, chondroitin sulfate, keratin sulfate, and/or other extracellular matrix proteins, alginate, starch, cellulose, derivatives thereof, and the like. In preparing the compositions of the present disclosure, the non-cross-linked polymers are typically first suspended in a suitable medium, typically an aqueous medium, having suitable buffers, secondary binders, additives, preservatives, antioxidants, bioactive agents, or the like, added. Once the non-cross-linked polymer is suspended at a suitable concentration, typically in the range from 0.2 weight % to 10 weight %, and in one preferred embodiment from 0.25 weight % to 2 weight %, the cross-linked polymer will be added, typically in a dry particle form. After the dispersion of the cross-linked polymer has been well mixed in the solution of the non-cross-linked polymer, the suspension may be dried by any conventional technique. For example, the medium can be spread in a thin layer, typically from 1 mm to 50 mm, depending on the solids concentration in the medium, and lyophilized to produce a dry material (for example, a sponge-like material) which may then be sterilized and used in the methods described herein below. Alternatively, the solution of non-cross-linked polymer may be sterile filtered and combined in a sterile environment with the cross-linked polymer sterilized by other means and be subjected to processing carried out under aseptic conditions. Sterilization may occur via electronic-beam, γ-irradiation, or via ethylene oxide or other chemical sterilant, or the like. Preferred suitable drying techniques include air drying, heat drying, spray drying, fluid-bed drying molding, or the like. The materials may be formed into particles of various geometries, such as powder granules, pellets, plugs, cylinders, half-cylinders, tubes, spheres, spheroids, irregular granules or particles, or the like for specific uses. The compositions of the present disclosure may be further combined with other materials and components, e.g., anti-caking agents, flow-enhancing agents, anti-static agents, and the like, such as zinc stearate, carbohydrates and alcohols, and other materials intended for other purposes, such as to control the rate of resorption.

The compositions of the present disclosure do not contain an active agent, such as thrombin. Exemplary active agents may include, but are not limited to, inorganic and organic biologically active molecules such as enzymes, enzyme inhibitors, antibiotics, antineoplastic agents, bacteriostatic agents, bactericidal agents, antiviral agents, hemostatic agents (e.g., thrombin, fibrinogen and clotting factors), local anesthetics, anti-inflammatory agents, hormones, anti-angiogenic agents, antibodies, neurotransmitters, psychoactive drugs, drugs affecting reproductive organs and oligonucleotides, such as antisense oligonucleotides, or inorganic components such as hydroxyapatite, and ferric chloride.

The biologically compatible polymer compositions of the present disclosure may be mechanically disrupted prior to their final use or delivery. Molecular cross-linking of the polymer chains of the polymer composition can be performed before or after its mechanical disruption. For example, the product may be ground after gelatin extraction and reground after cross-linking. The polymer compositions may be mechanically disrupted in batch operations, such as mixing, so long as the polymer composition is broken down into sub-units having a size in the 0.01 mm to 5.0 mm range set forth above. When the polymer composition is disrupted prior to use, the polymer particles or granules can be applied or administered by techniques other than extrusion or spraying from a syringe orifice e.g., using a spatula, spoon, or the like. Other batch mechanical disruption processes include pumping through a homogenizer or mixer or through a pump which compresses, stretches, or shears the hydrogel to a level which exceeds a fractural yield stress of the hydrogel. In some cases, extrusion of the polymeric composition causes the hydrogel to be converted from a substantially continuous network, i.e., a network which spans the dimensions of the original hydrogel mass, to a collection of sub-networks or sub-units having dimensions in the ranges set forth above. In other cases it may be desirable to partially disrupt the hydrogel compositions prior to packaging in the syringe or other applicator. In such cases, the hydrogel material will achieve the desired sub-unit size prior to final extrusion.

In an embodiment, the polymer may be initially prepared (e.g., by spray drying) and/or be mechanically disrupted prior to being cross-linked, often usually prior to hydration to form a hydrogel. The polymer may be provided as a finely divided or powdered dry solid, which may be disrupted by further comminution to provide particles having a desired size, usually being narrowly confined within a small range. Further size selection and modification steps, such as sieving, cyclone classification, etc., may also be performed. For the exemplary gelatin materials described hereinafter, the dry particle size may be in the range from 0.01 mm to 1.5 mm, and in one preferred embodiment from 0.05 mm to 1.0 mm. An exemplary particle size distribution is such that greater than 95% by weight of the particles are in the range from 0.05 mm to 0.7 mm. Methods for comminuting the polymeric starting material include homogenization, grinding, coacervation, milling, jet milling, and the like. Powdered polymeric starting materials may also be formed by spray drying. The particle size distribution may be further controlled and refined by conventional techniques such as sieving, aggregation, further grinding, and the like.

The dry powdered solid may then be suspended in an aqueous buffer, as described elsewhere herein, and cross-linked. In other cases, the polymer may be suspended in an aqueous buffer, cross-linked, and then dried. The cross-linked, dried polymer may then be disrupted, and the disrupted material subsequently resuspended in an aqueous buffer. The resulting material in one embodiment comprises a cross-linked hydrogel typically having discrete sub-networks having the dimensions set forth above.

The compositions of the present disclosure are particularly suitable for inhibiting bleeding (causing hemostasis) on an abraded or damaged tissue surface, e.g., any organ surface including the liver, spleen, heart, kidney, intestine, blood vessels, vascular organs, and the like. A granule or other form of the dried material is applied so that the active bleeding area is completely covered with the material. For example, a delivery device or delivery system described herein, containing powder granules, may be used to apply the material to the active bleeding area. Suitable methods for applying the material include, but are not limited to, dispensing the material directly from the syringe or using an applicator tip. Prior to applying the powder granules, the bleeding tissue generally is blotted or gently suctioned to remove excess blood so that the powder granules can be applied immediately and directly to the site of active bleeding. Clogging of the syringe and/or applicator tip or other device can be reduced by minimizing contact of the syringe or applicator tip to wet surfaces. Similarly, particular configurations of the delivery device or delivery system can serve to prevent clogging. After the powder granules are applied, wound-appropriate, gentle approximation typically is applied over the treated site using a non-adhering substrate such as moistened gauze. Additional powder granules may be applied if bleeding persists. If the non-adhering substrate adheres to the wound site, gentle irrigation with non-heparinized saline may be used to aid in removal of the substrate with minimal disruption to the clot. Once bleeding has ceased, excess granules not incorporated into the clot are carefully removed by gentle irrigation and suction away from the treatment site.

When used in regions surrounding nerves and other sensitive body structures, fully hydrated hydrogels (i.e., with >95% of hydration at equilibrium swell) may be employed to reduce the risk of damage to the nerves from swelling in an enclosed environment.

Kits according to the present disclosure may comprise a granule or other form of the dried polymeric material of the present disclosure, such as pellets, powder, or the like. The materials are formed sterilely or will be sterilized, preferably by terminal sterilization using γ-irradiation, ethylene oxide, electronic beam irradiation, and the like. While still in a sterile form, the materials will be packaged in a sterile package, such as a pouch, tube, tray, box, or the like. Instructions for use setting forth a method of placing the material over tissue in the presence of blood, e.g., at a wound, or surgical site, may also be provided as part of the kit. An exemplary kit includes the dried polymeric material (e.g., dry bovine-derived gelatin matrix (granules)) present in a syringe, an applicator tip, a delivery device described herein configured to be used with the syringe, and instructions for use.

Delivery Device and Delivery System

Referring now to FIG. 1, one suitable delivery system, and associated methods and devices for accurately delivering any of the compositions discussed above, is illustrated by system 100. Delivery system 100 includes a syringe 110 and a spring cap assembly 120 operably coupled to syringe 110. For this disclosure, the spring cap assembly 120 herein may be referred to interchangeably as a delivery device. Syringe 110 includes a plunger 112 and a barrel 114. Plunger 112 is sited to concentrically engage and seal with the inner cylindrical surface of barrel 114, such that the plunger 112 may translate along a length of the barrel 114. Each of plunger 112 and barrel 114 may be constructed of any suitable plastic material, such as polypropylene, PVC, non DEHP PVC, polyethylene, polystyrene, polypropylene mixture, or other similar materials. Preferably, each of the plunger 112 and barrel 114 are constructed of polypropylene.

Figure 9:
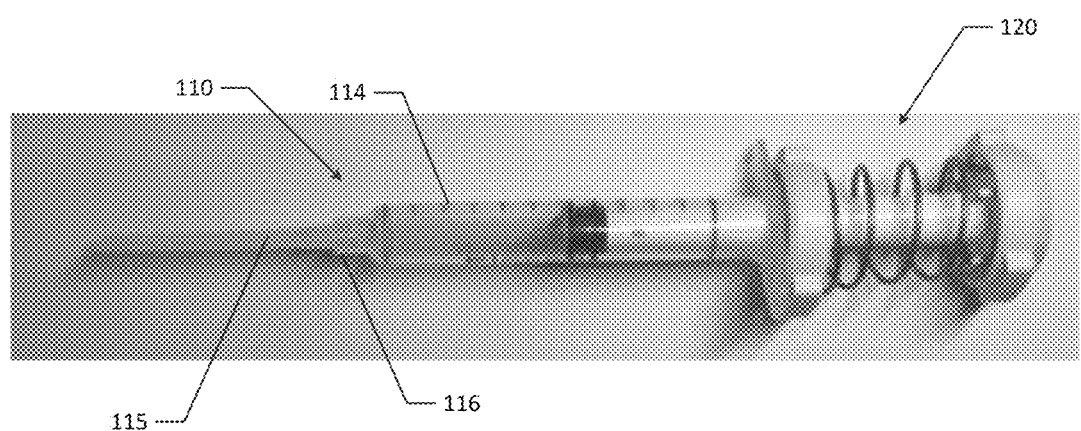
FIG. 9 is a side view of a delivery system, including a delivery device, a syringe, and an extension tip, according to an example embodiment of the present disclosure.

Syringe barrel 114 defines an orifice 116 at its distal end. In an example embodiment, orifice 116 includes a luer tip, such as a female-luer connector or a male-luer connector. Syringe 110 is configured to expel a material through orifice 116. For example, syringe 110 is configured to expel a biologically compatible polymer that forms a hydrogel when exposed to blood, as described above. Referring to FIG. 9, in an example embodiment, syringe 110 may further include an extension tube 115, configured to engage the orifice 116 of syringe barrel 114, e.g., via a luer connection. The extension tube 115 may improve delivery accuracy in both open procedures and laparoscopic procedures, e.g., where access to a wound-site is limited. In various embodiments, the extension tube 115 may be a rigid extension tip, a trimmable extension tip, a flexible tip, a malleable tip, etc.

Spring cap assembly 120 includes a retainer ring 122, a cap 124, and a spring 126. The spring 126 may be formed from steel, stainless steel, aluminum, titanium, and alloys thereof, and may be disposed between retainer ring 122 and cap 124, such that spring 126 is retained by retainer ring 122 and cap 124. Spring 126 may have a spring force constant in the range of 1 to 10 pound-force. More preferably, spring 126 may have a spring force constant of 3.46 pound-force. In an embodiment, spring 126 has a 1.2 inch diameter, a 1.75 inch free length, and is constructed of a stainless steel wire with a 0.0625 inch diameter. Spring 126 in the illustrated embodiment is a compression spring, such that spring 126 biases cap 124 away from retainer ring 122.

Figure 7A:
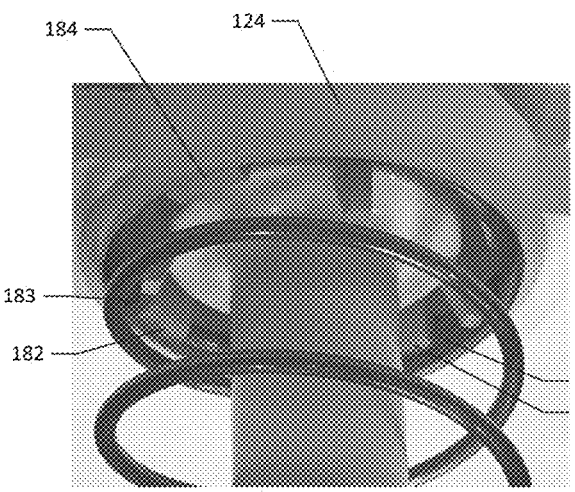
FIGS. 7A to 7B are perspective views of a cap and a spring, according to an example embodiment of the present disclosure.
Figure 7B:
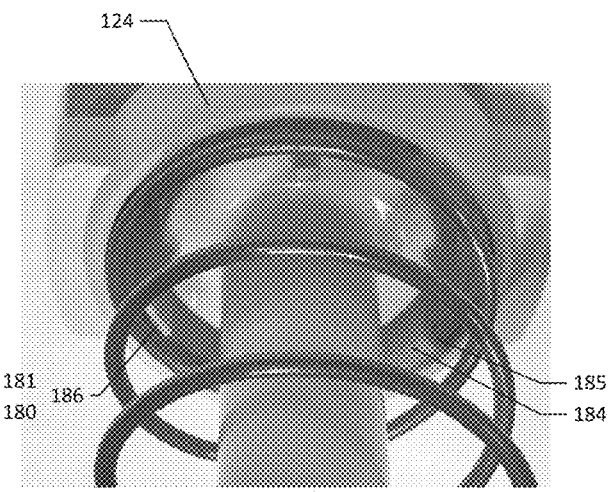
Figure 8A:
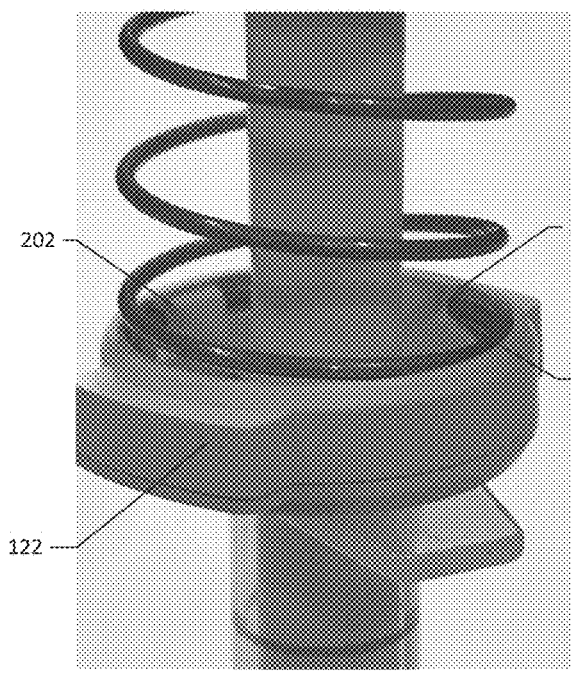
FIGS. 8A to 8B are perspective views of a retainer ring and a spring, according to an example embodiment of the present disclosure.
Figure 8B:
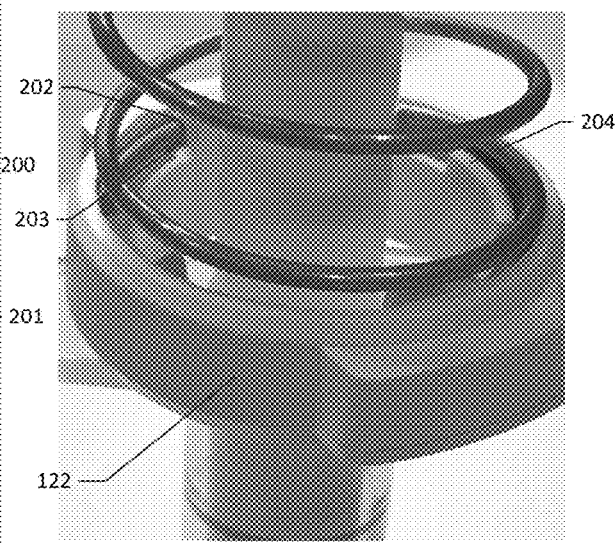

Referring now to FIGS. 7A, 7B, 8A, and 8B, an inner detailed perspective of the cap 124 (FIGS. 7A, B) and the retainer ring 122 (FIGS. 8A, B) are illustrated and discussed. Retainer ring 122 includes a plurality of clips 200, 202 for receiving one ring circle of spring 126, to retain one end of spring 126. In various embodiments, clips 200, 202 are features of the molded retainer ring 122 that extend from the inner peripheral wall of the retainer ring 122 axially inward to retain the spring 126. When formed on the retainer ring 122, the clips 200, 202 define an opening through which the spring 126 is received. It should be appreciated that, as shown in FIGS. 8A and 8B, the opening through which the spring 126 is received is defined by clips 200, 202 on the top and side of the spring 126, and also includes lower surfaces 201 and 203, which defines a lower resting surface for the spring 126 to reside, opposite clips 200, 202, respectively. In various embodiments, the clips define one, two or more sides of the opening through which the spring 126 is received. For example, member 204 illustrated in FIG. 8B shows only a single-retention extrusion that retains the spring 126 against the inner peripheral wall of the retainer ring 122, but does not define a substantially enclosed opening to receive the spring 126 itself. It should be appreciated that the retainer ring 122 could include any appropriate number of clips 200, 202 or members 204 around its periphery. The illustrated embodiment includes one member 204 and three clips similar to 200 and 202, spaced around the circumference of the retainer ring 122.

In various embodiments, each of the plurality of clips 200, 202 may be configured to snap-fit over the end of the spring 126. It should be appreciated that, due to the axial angle of pitch of the spring 126 the interference between the clips 200, 202 and the respective lower surfaces 201, 203 of the retainer ring 122, the spring's friction fit inhibits its rotational displacement once received by each of the peripheral clips 200, 202 or member 204.

As seen in FIGS. 7A and 7B, and similar to the features discussed above in reference to the retainer ring 122 in FIGS. 8A and 8B, cap 124 also includes a plurality of clips 180, 182, 184 for receiving a ring circle at the opposing end of spring 126 to retain the other end of spring 126. Each of the plurality of clips 180, 182, 184 may be configured to snap-fit over the respective ends of spring 126 and/or include at least one recess or void, configured to receive a portion of spring 126 for retaining spring 126. Like the clips 200, 202 in FIGS. 8A and 8B, each of the plurality of clips 180, 182, 184 may include frictional fitting or additional mechanical engagement with spring 126, such as a mechanical press-fit, or ultrasonic welding. As seen in FIG. 7A, clip 180 defines an opening or passage through which the top portion of spring 126 is received. The opening is defined by clip 180 as well as upper surface 181, which extends from the inside surface of the top of the cap 124. Similarly, clips 182 and 184 each define openings with respective upper surfaces 183, 185 extending from the inside surface of the top of the cap 124. Each of upper surfaces 181, 183, 185 provide an abutment surface against which the spring 126 rests when received by the openings defined by clips 180, 182, 184. It should be appreciated that cap 124 also includes member 186, which extends downward (along an axial direction of the spring 126, when assembled) from the inside surface of the top of cap 124. In various embodiments, the function of member 186 of FIG. 7B is analogous to the function of member 204 illustrated in FIG. 8B and discussed above.

For each of cap 124 and retainer ring 122, each of the plurality of respective illustrated clips and members (180, 182, 184, 186, 200, 202, 204) are configured to cooperate to retain each of the two ends of spring 126, and ensure that spring 126 is mechanically attached to each of the retainer ring 122 and cap 124. As discussed above, any suitable number of clips or members can be employed to ensure a snug fit, and this disclosure is not meant to limit these features to the precise number, design, and configuration of those illustrated and discussed herein. Each of the plurality of clips and members (180, 182, 184, 186, 200, 202, 204) work together to prevent spring 126 from rotating during use by securely affixing the opposite ends of spring 126 to each of the retainer ring 122 and cap 124, respectively. By affixing spring 126 to each of the retainer ring 122 and cap 124, the entire spring cap assembly 120 may be prevented from axial rotation and also accidental disassembly. In an embodiment, retainer ring 122 and cap 124 are generally restricted from rotating axially. This may ensure, for example, a more rigid spring cap assembly 120, which may be beneficial when attaching the spring cap assembly 120 to syringe 110.

Figure 10:
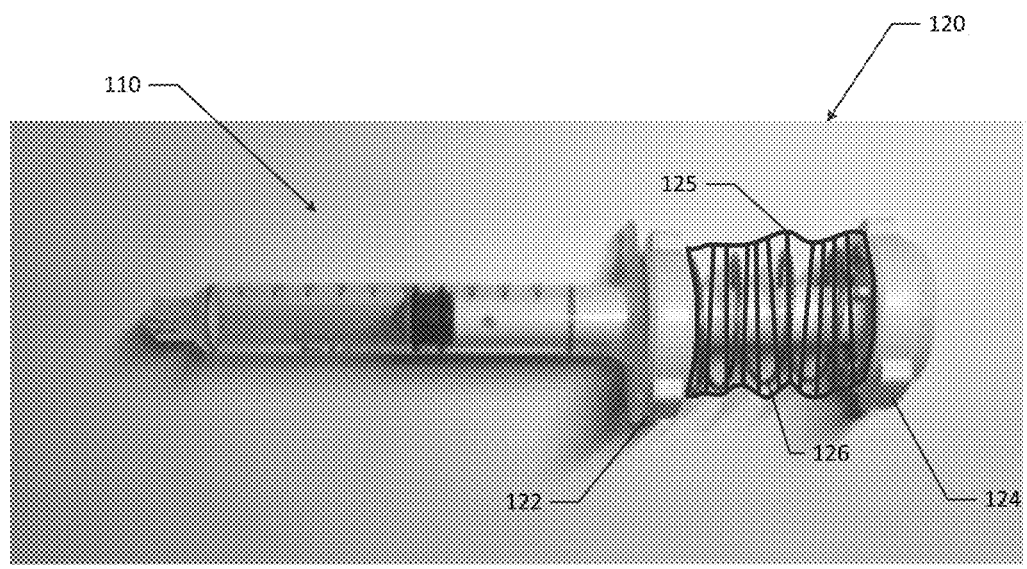
FIG. 10 is a side view of a delivery system, including a delivery device, a syringe, and a wrap, according to an example embodiment of the present disclosure.

Referring to FIG. 10, in an embodiment, spring 126 includes a wrap 125, such as a flexible plastic wrap, flexible cloth wrap, etc. In various embodiments, the wrap 125 may cover the spring 126 to prevent a portion of the spring 126, or the entire spring 126, from environmental exposure. For example, the wrap 125 may cover the entire exterior circumference and length of spring 126, such that the wrap 125, the retainer ring 122, and the cap 124 form a compressible cylinder, with spring 126 disposed inside the compressible cylinder. Wrap 125 illustrated in FIG. 10 is semi-transparent, to illustrate the spring 126 disposed inside. In various embodiments, wrap 125 may be transparent, semi-transparent, or opaque.

Figure 2:
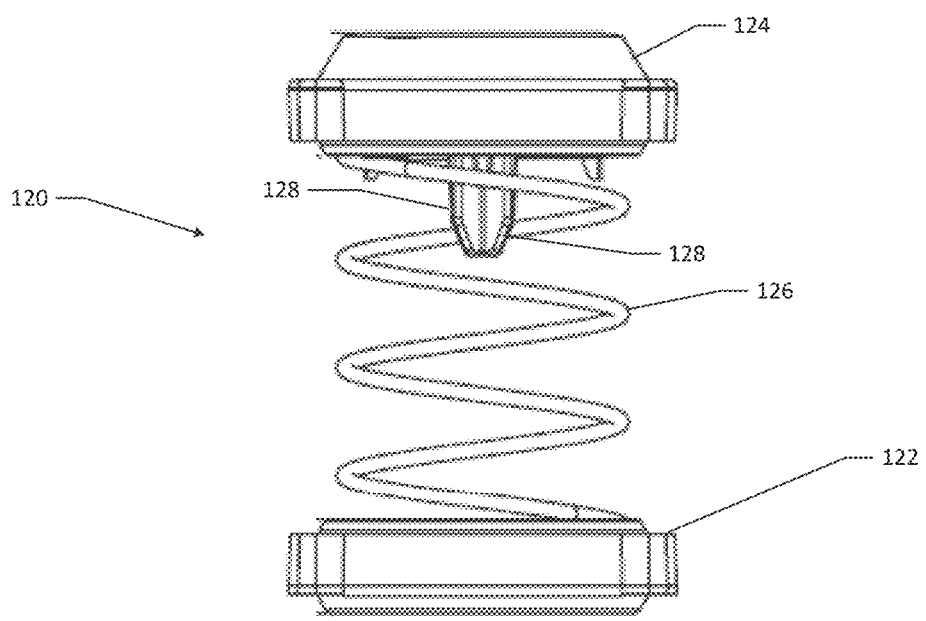
FIG. 2 is a side view of a delivery device, according to an example embodiment of the present disclosure.

FIG. 2 illustrates that a post 128 extends from cap 124. Post 128 is configured to engage with a proximal capped end of plunger 112 of the syringe 110. In one embodiment, the proximal end of the plunger 112 may be provided with a receptacle for receiving and/or snapping to post 128. Post 128 may provide stability, e.g., via a loose interference fit, to reduce lateral movement, shaking, etc. between spring cap assembly 120 and plunger 110. In an example embodiment, post 128 is formed integrally within cap 124. For example, the post 128 and the cap 124 may be injection molded as one piece of material, such as polypropylene, PVC, non DEHP PVC, polyethylene, polystyrene, polypropylene mixture, or other similar materials. As illustrated in FIG. 2, post 128 extends along the central axis of spring 126 towards the retainer ring 122. Post 128 is disposed concentrically within the spring 126 in one embodiment.

Figure 3:
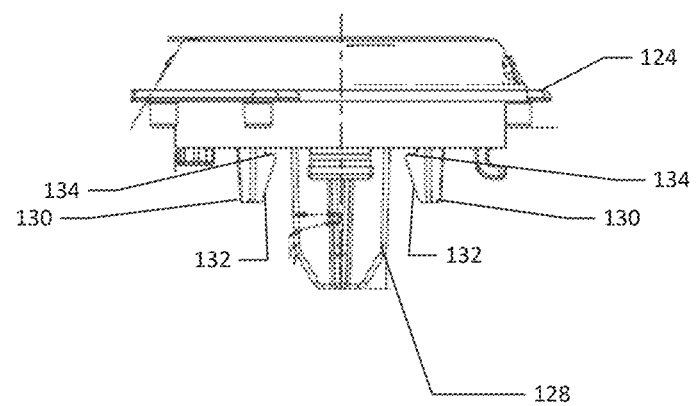
FIG. 3 is a side view of a cap, according to an example embodiment of the present disclosure.

FIG. 3 illustrates the cap 124, including the post 128 in more detail. As previously noted, the proximal end of the plunger 112 in one embodiment includes a receptacle configured to receive the post 128. The receptacle ensures that only approved syringes (e.g., syringe 110) may be used with spring cap assembly 120. A non-compliant syringe that does not include the receptacle will not be able to receive the post 128 and therefore cannot be used with spring cap assembly 120.

Referring specifically to FIGS. 3 and 5A to 5C, cap 124 further includes a plurality of latch arms 130. For example, each of the plurality of latch arms 130 extends from an inner surface of the cap 124. Each of the plurality of latch arms 130 includes an angled cam surface 132. For example, each of the latch arms 130 may have a surface that slopes downward (e.g., toward the inner surface of the cap 124) and inward (e.g., towards the center point of cap 124). This angled cam surface 132 may ensure, for example, proper deflection when the plurality of latch arms 130 engage with the plunger 112 of the syringe 110. Each of the plurality of latch arms 130 includes a latching shoulder 134. For example, the latching shoulder 134 defines a latch surface opposing the inner surface of the cap 124. The cap may further include members 131 having surface 138 (e.g., raised step surfaces) projecting from the inner surface of the cap 124. These members 131 may provide for cooperatively locking of the plunger 112 (e.g., a flanged end of the plunger 112) between the latch surface of latching shoulder 134 and the surface 138 of members 131. In this way, the plurality of latch arms 130 may securely engage the cap 124 to the plunger 112 of the syringe 110. It should be appreciated that the axial distance measured between the latching shoulder 134 and the raised member surface 138 is approximately the same as the thickness 118A of the flanged end 118 of plunger 112, accommodating for a reasonable tolerance, to achieve secure retention of the flanged end 118 of plunger 112 within the cap 124.

For example, when a flanged end 118 of the plunger 112 abuts the plurality of latch arms 130 (e.g., abutting the angled cam surface 132), the plurality of latch arms 130 flex outwardly (e.g., away from the center point of cap 124). Once the flanged end 118 of the plunger 112 passes the latching shoulder 134, the plurality of latch arms 130 flex inwardly (e.g., toward the center point of cap 124). During the inward flexing of the plurality of latch arms 130, the user may experience a tactile "snap." Likewise, the user may experience an audible "snap." These snaps serve to indicate, to a user, that the flanged end 118 of the plunger 112 is retained within the cap 124 by the plurality of latch arms 130. At this point, the flanged end 118 of the plunger 112 is retained securely between the latching shoulder 134 of the plurality of latch arms 130 and the member surfaces 138 (e.g., raised step surfaces) of members 131 of the cap 124.

In an example embodiment, latch arms 130 are formed integrally with the cap 124. For example, latch arms 130 and cap 124 may be injection molded as one piece of material, such as polypropylene, PVC, non DEHP PVC, polyethylene, polystyrene, polypropylene mixture, or other similar materials. Each of the plurality of latch arms 130 is configured to engage and snap-fit over the proximal end of the plunger 112. For example, the outer edge of the capped end of the plunger 112 may be snap-fitted within the plurality of latch arms 130, such that the proximal end 118 of the plunger 112 is retained inside the plurality of latch arms 130. In the described and illustrated embodiments, four latch arms 130 are employed to secure proximal end 118 of plunger 112, but it should be appreciated that any suitable plurality of latch arms 130 can be implemented to achieve the desired plunger retention function described herein. Cap 124 may further include indentations, protrusions, grips, or other features, configured to improve a user's finger grip and prevent slippage and mishandling.

Figure 4:
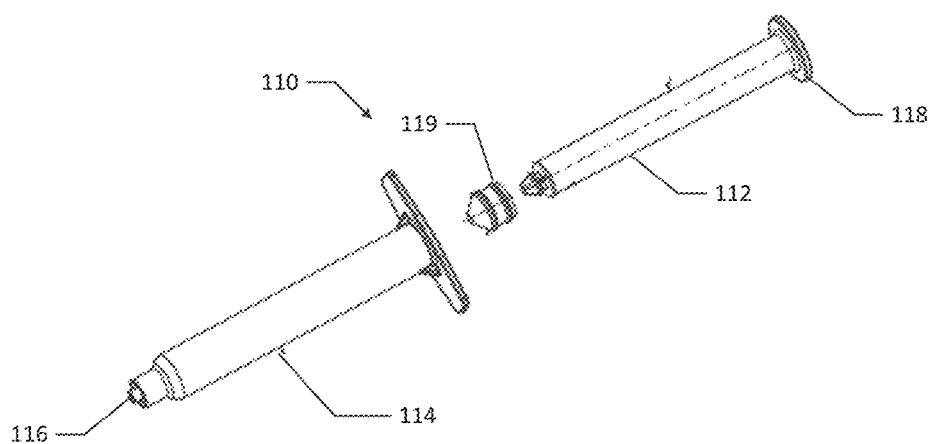
FIG. 4 is a perspective view of a syringe, according to an example embodiment of the present disclosure.

FIG. 4 illustrates an exploded view of syringe 110, prior to engagement with spring cap assembly 120. Syringe 110 includes plunger 112, barrel 114, and connector having orifice 116. FIG. 4 further illustrates a circular proximal end 118 of plunger 112. As previously described, the outer edge of the circular proximal end 118 of thickness 118A of the plunger 112 is, in one embodiment, received by the plurality of latch arms 130 of spring cap assembly 120 to retain proximal end 118 of the plunger 112 inside the plurality of latch arms 130.

As illustrated in FIG. 4, the distal end of plunger 112 is fitted with a medical grade stopper 119, e.g., a silicone stopper, which seals to the inside cylindrical wall of barrel 114 to push the compositions of the present disclosure out through orifice 116. In one embodiment, the medical grade stopper 119 is constructed of SANTOPRENE TPV® thermoplastic elastomer or, alternatively, of any other suitable material. While plunger 112 includes the medical grade stopper 119, in certain embodiments an increase in air pressure generated within barrel 114 physically pushes out the composition. Similarly, in certain embodiments, a decrease in air pressure generated within the barrel 114 draws air into the barrel to unclog orifice 116.

FIGS. 5A to 5C illustrate one embodiment for engagement between cap 124 and plunger 112. The flanged proximal end 118 of plunger 112 includes or defines a receptacle 136. Cap 124 includes post 128, which is configured to be received by receptacle 136. In an embodiment, post 128 and receptacle 136 have a same cross-sectioned shape, so as to engage with one another in a loose interference fit. Likewise, each of the plurality of latch arms 130 is configured to engage, e.g., via outwardly bending spring-like deformation illustrated in FIG. 5B, and snap-fit over the proximal end 118 of plunger 112, such that the proximal end 118 of the plunger 112 is retained inside the plurality of latch arms 130, as illustrated by FIG. 5C and previously described herein. It should be noted, in FIG. 5C, that proximal end 118 of plunger 112 abuts up against members 131 and member surface 138 of cap 124, so that plunger 112 is constrained in both directions by cap 124 (e.g., the plunger 112 is locked in position for use with spring cap assembly 120).

As illustrated by FIG. 5C, cap 124 is configured to retain both spring 126 and the proximal end 118 of the plunger 112. As previously noted (and discussed above illustrated in FIGS. 7A, 7B), cap 124 includes the plurality of clips 180, 182, 184, which receive a ring circle at the end of spring 126 to retain the end of spring 126. Likewise, a plurality of clips 200, 202 on the retainer ring 122 (shown in FIGS. 8A, 8B) receive a ring circle at the other end of spring 126 to retain the other end of spring 126.

Figure 11A:
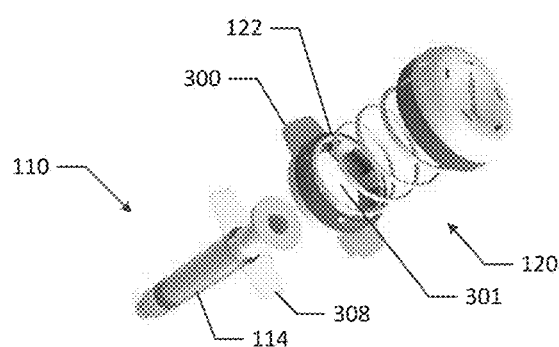
FIGS. 11A to 11B are perspective and side views of a delivery system, including a delivery device with a flanged collar and a syringe, according to an example embodiment of the present disclosure.
Figure 11B:
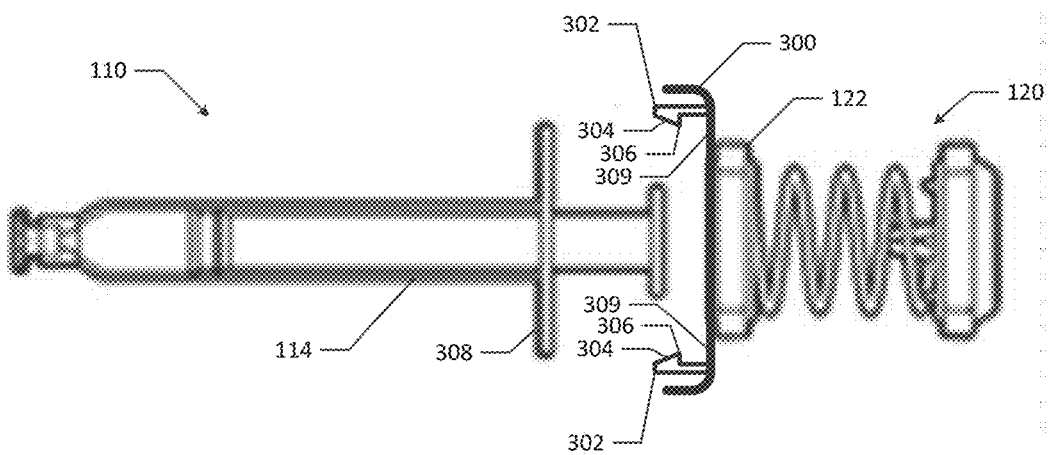

Referring to FIGS. 11A and 11B, in an alternative embodiment, spring cap assembly 120 may include different or additional features for engaging and retaining syringe 110. For example, the retainer ring 122 of spring cap assembly 120 may include a flanged collar 300. The flanged collar 300 is configured to engage with the end 308 of the barrel 114 of the syringe 110 (e.g., at the finger-holds on syringe 110). For example, the outer edge of the proximal end 308 of the barrel 114 may be press-fittingly received by the flanged collar 300, such that the proximal end 308 of the barrel 114 is retained inside the flanged collar 300. Flanged collar 300 includes a void 301 to ensure that certain portions of the syringe, such as plunger 112, may pass through a center of the flanged collar 300 uninterrupted.

Alternatively or additionally, flanged collar 300 may include a plurality of flange arms 302 for a snap-fit engagement (e.g., similar to the plurality of latch arms 130 on cap 124, as described above). Each of the plurality of flange arms 302 includes an angled cam surface 304. For example, each of the plurality of flange arms 302 may have a surface that slopes downward (e.g., toward an inner surface 309 of flanged collar 300) and inward (e.g., towards the center point of flanged collar 300). This angled cam surface 304 may ensure, for example, proper deflection when the plurality of flange arms 302 engage with the end 308 of the barrel 114 of the syringe 110. Each of the plurality of flange arms 302 includes a latching shoulder 306. For example, the latching shoulder 306 defines a latch surface opposing an inner surface 309 of the flanged collar 300. In an embodiment, the proximal end 308 of the barrel 114 is cooperatively locked between the latch surface of the latching shoulder 306 and the inner surface 309 of the flanged collar 300. In this way, the plurality of flange arms 302 may securely engage the flanged collar 300 and the retainer ring 122 to the barrel 114 of the syringe 110. Flanged collar 300 may be formed integrally with retainer ring 122. Retainer ring 122 may alternatively or additionally include apertures that snap fittingly receive members extending from, e.g., integrally formed with, the proximal end 308 of the barrel 114.

Figure 12:
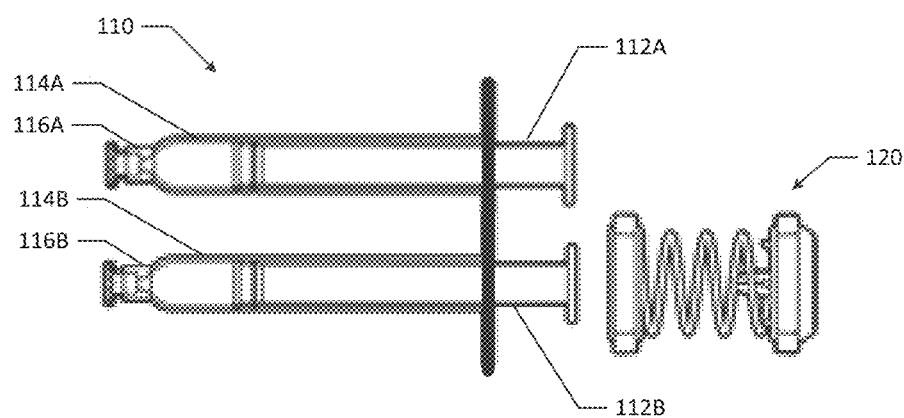
FIG. 12 is a side view of a delivery system, including a delivery device and a dual-barrel syringe, according to an example embodiment of the present disclosure.

Referring to FIG. 12, in an alternative embodiment, the barrel 114 of syringe 110 includes at least a first compartment 114A and a second compartment 114B (e.g., a dual-barrel syringe). For example, the barrel 114 may retain a first material in the first compartment 114A and a second material in the second compartment 114B. Each of the first compartment 114A and the second compartment 114B may be aligned in parallel, such that an orifice 116A, 116B is provided for each of the first compartment 114A and the second compartment 114B. Alternatively, both compartments 114A, 114B may flow into communication with a single orifice (not shown). Likewise, plunger 112 or separate plungers 112A, 112B may engage with each of the first compartment 114A, the second compartment 114B, and spring cap assembly 120. In this embodiment, the spring cap assembly 120 may be used with each plunger 112A, 112B individually. For example, the spring cap assembly 120 may be attached to the plunger 112A for the first compartment 114A, used to deliver material from the first compartment 114A, detached from the plunger 112A for the first compartment 114A, attached to the plunger 112B for the second compartment 114B, and used to deliver material from the second compartment 114B.

In an alternate embodiment where one plunger engages with both the first compartment and the second compartment, a single spring cap assembly 120 may be used to deliver both materials simultaneously. In this alternate example embodiment, the first material and the second material may be prevented from mixing in the barrel 114; rather, the first material and the second material may mix at the orifice 116 or may mix once expelled form the syringe 110. Further alternatively, first and second materials may be stacked back-to-back in the same barrel 114, wherein a first one of the materials flows out of orifice 116 before the second material flows out of orifice 116.

Figure 13:
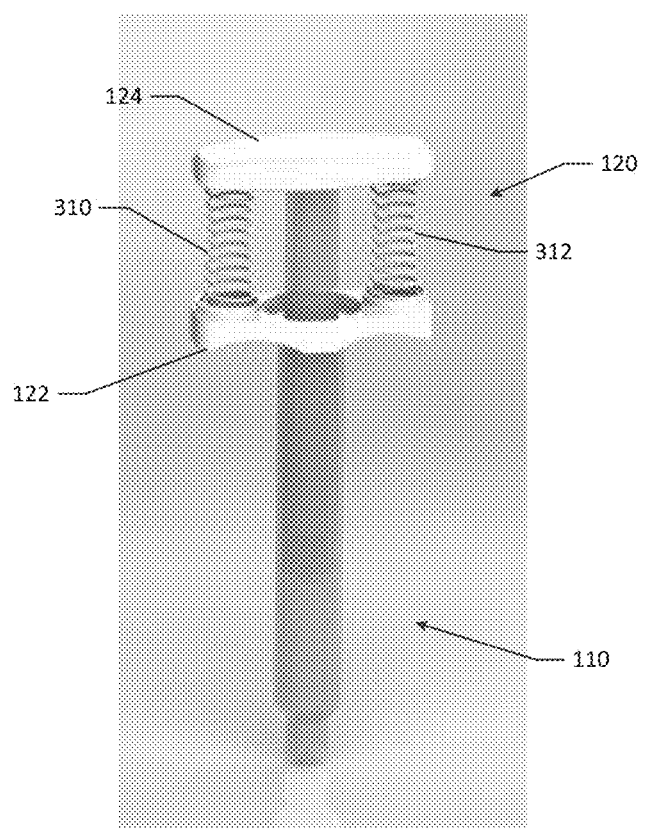
FIG. 13 is a perspective view of a delivery system, including a dual-spring delivery device and a syringe, according to an example embodiment of the present disclosure.

Referring to FIG. 13, in another alternative embodiment, a single spring cap assembly 120 may implement several springs. For example the spring cap assembly 120 may include a first spring 310 and a second spring 312, each of which are disposed between the cap 124 and the retainer ring 122. In an embodiment, one of the at least two springs is configured to concentrically receive the plunger 112 (as described above). In a different embodiment (as depicted in FIG. 13), neither of the at least two springs 310, 312 is configured to concentrically receive the plunger 112.

By implementing spring cap assembly 120 with syringe 110, improved surgical results are achieved. It is first believed that dispersion accuracy is improved. For example, users may deliver compositions to targeted areas in a controlled fashion, using one-handed delivery. Second, it is believed that delivery efficiency is improved. For example, certain current powdered delivery devices implement an accordion, bellows-type configuration (e.g., ARISTA™ AH). Accordion, bellows-type configurations often result in powder being trapped within the accordion folds. By eliminating the accordion-bellows configuration, spring cap assembly 120 and syringe 110 help to ensure that no powder is trapped; rather, most or all powder is expelled in an efficient manner. For example, more powder is dispensed with each expression or pump. In one embodiment, all powder is dispersed over several (e.g., ten) pumps of syringe 110. In an alternate embodiment, all powder is dispersed in one pump of syringe 110. Third, spring cap assembly 120 provides for use with several syringes. For example, spring cap assembly 120 can be attached to a first syringe, used with the first syringe, removed from the first syringe, attached to a second syringe, and used with the second syringe. This may increase surgical efficiency, decrease costs, etc.

Method of Administering a Polymeric Composition

FIGS. 6A to 6C illustrate one example method for using spring cap assembly 120. FIGS. 6A and 6B illustrate the coupling of cap 124 of the delivery device to the plunger 112 of the syringe 110 to create a new and improved powder hemostat delivery system 100. As shown in both FIGS. 6A and 6B, barrel 114 of syringe 110 comes pre-loaded with a powdered material 602.

As previously described, cap 124 may include post 128. The user snap-fittingly inserts post 128 of cap 124 into the proximal end 118 of the plunger 112. As illustrated, the user may slide the plunger 112 through the retainer ring 122 and through the spring 126. The user aligns the post 128 with the mating receiving aperture of plunger end 118. The user then firmly presses cap 124 onto the end 118 of the plunger 112, until the cap 124 snaps onto the plunger 112. FIG. 6B illustrates that spring cap assembly 120 is coupled to the syringe 110, where the user may hear an audible click, feel tactile feedback related to the click, or both.

Spring cap assembly 120 is properly connected to syringe 110 when the plunger 112 retracts due to expansion of spring 126. As illustrated in FIG. 6C, a new and improved hemostat delivery system 100, including syringe 110, with powdered material 602, such as hemostat particles, in barrel 114, and spring cap assembly 120, is ready for use. The user may then depress cap 124 of the spring cap assembly 120 to deliver powdered material 602 (e.g., any one or more of the compositions described above). Responsive to depressing cap 124, the spring 126 of the spring cap assembly 120 compresses and plunger 112 translates towards the connector 116 at the distal end of the syringe 110. Depressing cap 124 causes powdered material 602 to aspirate from syringe 110 (e.g., due to increased air pressure in barrel 114). In an embodiment, fully depressing cap 124 to fully compress spring 126 requires approximately 5 pounds of force. For example, a user is able to fully depress cap 124 to fully compress spring 126 with one hand.

The user may then release cap 124 of spring cap assembly 120. Responsive to releasing cap 124, spring 126 of the spring cap assembly 120 expands. Likewise, the plunger 112 translates toward the proximal end of the syringe 110. The user may continually depress and release the cap 124 as the powdered material 602 is expelled from the distal end of the syringe 110. This may ensure that powdered material 602 is delivered from the syringe in a controlled manner. This may further ensure that powdered material 602 does not clog at the distal end of the syringe 110. For example, when spring 126 of spring cap assembly 120 expands, syringe 110 may "reload" itself via air flow into barrel 114 (e.g., due to reduced air pressure in barrel 114). In an embodiment, powdered material 602 is dispersed over ten pumps of syringe 110.

In one embodiment, the user may continually depress and release the cap 124, until all of powdered material 602 is expelled from the distal end of the syringe 110. In a related embodiment, the user may subsequently detach the spring cap assembly 120 from syringe 110, attach spring cap assembly 120 to a new syringe, and expel material from the new syringe. In this way, the spring cap assembly 120 may be used for the delivery of several quantities of material across several syringes and/or delivery of several types of material across several syringes. In an alternate embodiment, the user may implement spring cap assembly 120 and syringe 110 intermittently. For example, the user may expel a first portion of powdered material 602 from syringe 110 at a first time, using spring cap assembly 120, but may not require all of the powdered material 602 within syringe 110 at the first time. With spring cap assembly 120, there is no use time constraint. Therefore, the user can subsequently expel a second portion of powdered material 602 from syringe 110 at a second time, using spring cap assembly 120.

In an example embodiment, the syringe 110 comes pre-loaded with the material to-be-delivered (e.g., powdered material 602). Typically, this may mean that the powdered material 602 is in a compact form (e.g., compacted powder). When the syringe 110 comes pre-loaded, the syringe 110 may initially include a plug, fastened to the luer tip of orifice 116. In this embodiment, a user may couple the cap 124 of the spring cap assembly 120 to the plunger 112 of the syringe (as described above). Once the spring cap assembly 120 is attached to plunger 112, the spring cap assembly 120 will retract plunger 112, due to expansion of spring 126. This creates an initial air gap, which is a vacuum or negative pressure air gap, within barrel 114. The user may then remove the plug from the orifice 116. By removing the plug from orifice 116, air immediately flows into the barrel 114, filling the air gap (e.g., via the pressure differential between the environment and the vacuum or negative pressure air gap). This initial flow of air may serve several purposes. For example, the initial flow of air may serve to break-up compacted powder. Also, for example, the initial flow of air is directed into the barrel 114; thus, the initial flow of air may prevent inadvertent powder from spilling out of the orifice 116. The user may then begin depressing and releasing the cap 124 to expel powdered material 602 from the distal end of the syringe 110 (as described above).

It should be appreciated that the length of the sub-assembly of a syringe plunger 112 and its stopper 119 in typical medical syringes is approximately equal to the length of the barrel 114. As a user advances the plunger 112 with respect to the barrel 114, the stopper 119 pushes the contents of the barrel 114 out of the orifice 116, and it is desirable that the stopper 119 travels to a point in complete abutment with the seat 117 (See FIG. 6B) adjacent to the orifice 116 to ensure maximum delivery quantity and minimize hold-up waste. In the presently-discussed syringe configurations, which include the cap 124/spring 126/retainer ring 122 assembly, it should be appreciated that, unless modified from a typical syringe, the length of the plunger 112 would be insufficient to allow the stopper 119 to completely abut with the interior seat 117 adjacent the orifice 116 when the cap 124 is depressed the maximum amount. Due to the axial width of the spring cap assembly 120 (including cap 124 plus the retainer ring 122 plus the compressed spring 126), a travel distance of length 121 of the plunger is used and therefore the stopper 119 is prevented from reaching abutment with seat 117, as desired. To compensate for the lost travel distance 121 of the plunger 112, occupied by the width 121 as determined by the spring cap assembly 120, several contemplated embodiments include a longer plunger 112 to ensure abutment of stopper 119 with seat 117 at the point of maximum depression of the spring cap 124 (as illustrated in FIG. 6B). It should be appreciated that it is not contemplated that distance 121 is equal to the total actual axial width of spring cap assembly 120, but rather the total additional length of plunger 112 occupied by engagement and maximum depression of the spring cap 124 and spring 126 when assembled as described and illustrated.

It should be appreciated that various medical applications for the system 100 may benefit from different quantities of material being expressed for each depression of the plunger. As discussed in Example 3 below, testing has determined that in one embodiment, over 95% of the desired total material was delivered within five expressions. It could, however, be advantageous or preferable in some situations to deliver the total quantity of material in fewer than five, six, seven, or more expressions. In such circumstances, it has been contemplated that the system 100 (or various subcomponents thereof) may be modified to purposely inhibit too-rapid delivery of the entire quantity of material than that described in Example 3. In other circumstances, the system 100 (or various subcomponents thereof) may be modified to allow a more rapid delivery of the entire quantity of material than that described in Example 3.

In some such embodiments, the orifice 116 is modified (expanded) to allow more material to pass with each depression of the plunger, thereby achieving total delivery in a fewer number of comparable expressions. In other embodiments, the orifice 116 is modified (restricted) to allow less material to pass with each expression of the plunger, thereby achieving total delivery in a greater number of comparable expressions. System 100 could also be modified to require more expressions to fully deliver the material by extending the length of the plunger 112 and by using a check valve near the orifice. It should be appreciated that various alternative techniques can be employed to more accurately control the quantity of necessary expressions required of a particular embodiment of the system 100 to deliver a target amount of material.

In various embodiments, and as discussed specifically with Example 3 below and FIG. 15, the powder or material delivered per expression can cover an area ranging from 1 $cm^2$ to 5 $cm^2$, with an average area of coverage of 3 $cm^2$. It should be appreciated that, when centered over the bleeding site, even with an average coverage of 3 $cm^2$, the focal delivery of the powder or material is concentrated on the bleeding site itself. In various embodiments, the focal point of the delivery includes a higher density of delivered powder or material (toward the center of the delivery area), and the periphery of the delivery area includes a relatively lower density of delivered powder or material. In some alternatives, and employing techniques altering the orifice geometry or amount of material delivered per expression, the density of delivered powder or material can be made more uniform or less uniform, depending upon the requirements of the particular medical application.

Delivery Device Kit

Figure 14A:
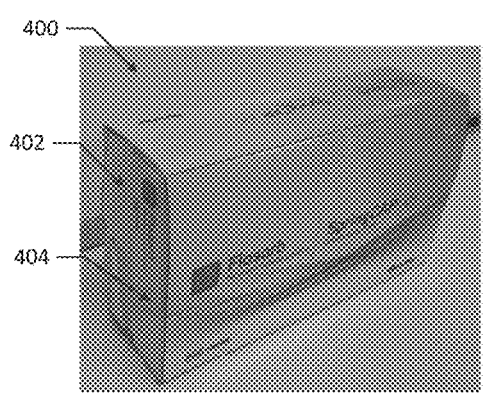
FIGS. 14A to 14C are perspective and side views of a delivery kit, including a pre-filled syringe and a delivery device, according to an example embodiment of the present disclosure.
Figure 14B:
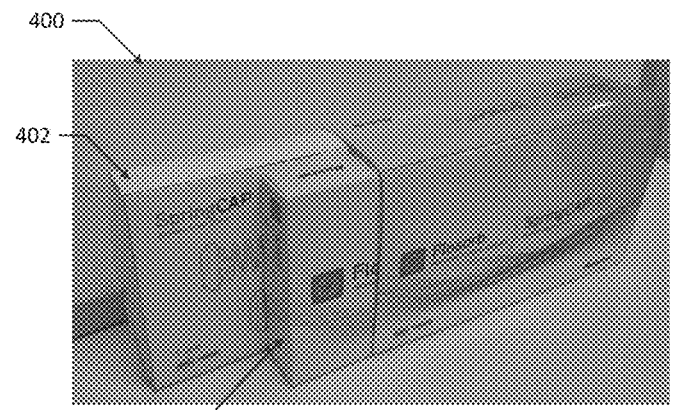
Figure 14C:
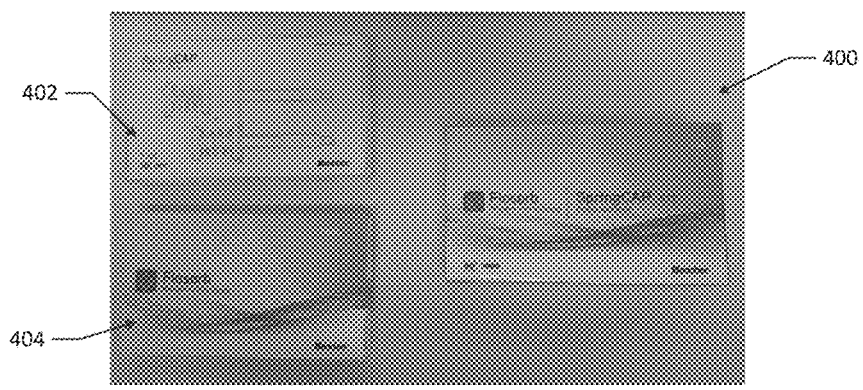

As illustrated in FIGS. 14A to 14C, the delivery device may be provided in a delivery kit 400. Delivery kit 400 may include both a spring assembly kit 402 and a powdered granule kit 404. In an embodiment, spring assembly kit 402 includes spring cap assembly 120, and powdered granule kit 404 includes syringe 110, which is pre-filled with powdered granules (e.g., dry particles of cross-linked bovine gelatin and non-crosslinked bovine gelatin). In a different embodiment, spring assembly kit 402 includes both spring cap assembly 120 and pre-filled syringe 110, and powdered granule kit 404 includes additional pre-filled syringes, additional powdered granules to re-fill syringe 110, other materials to be dispensed via syringe 110, etc. The components of delivery kit 400, including spring cap assembly 120, pre-filled syringe 110, and the powdered granules, are configured as described in greater detail above.

The following examples are offered by way of illustration, not by way of limitation.

EXAMPLES

Example 1—Hemostatic Efficacy of Powder Hemostat

The hemostatic efficacy of Powder Hemostat crosslinked gelatin to treat surgically-induced liver lesions in heparinized male domestic pigs was evaluated.

A hepatic square bleeding model was used for assessment of hemostatic success over a 10-minute period after treatment. Hemostatic success at 10 minutes after application was evaluated as to non-inferiority between Powder Hemostat and FLOSEAL® VH S/D (also known as FLOSEAL® HEMOSTATIC MATRIX VH S/D, FLOSEAL® HEMOSTATIC MATRIX, and FLOSEAL®) (Baxter Healthcare Corporation), a bovine-derived gelatin matrix combined with a human-derived thrombin solution. Hemostatic success at 10 minutes after application was also evaluated as to superiority of Powder Hemostat over ARISTA™ AH absorbable hemostatic particles, a thrombin-free hemostatic powder derived from purified plant starch. In addition, differences in the interval-censored time to hemostasis between Powder Hemostat and FLOSEAL® VH S/D and between Powder Hemostat and ARISTA™ AH were determined.

Powder Hemostat crosslinked gelatin consists of the same dry bovine-derived gelatin matrix (granules) present in FLOSEAL®.

FLOSEAL® VH S/D, was prepared according to the manufacturer's Instructions for Use (Baxter Healthcare Corporation, 2014). The thrombin solution was prepared by attaching the prefilled sodium chloride solution syringe to the luer connector of the vial adapter. Then, the rubber stopper of the thrombin vial was pierced, and all contents of the sodium chloride solution were transferred to the thrombin vial. The thrombin vial was then vented and swirled until the thrombin was completely dissolved. FLOSEAL® VH S/D was prepared by filling the empty 10 mL syringe with thrombin solution to the indicated mark (8 mL) and then connecting the gelatin matrix syringe to the syringe containing the thrombin solution. The thrombin solution was then passed into the gelatin matrix syringe, and the mixture was transferred back and forth between the syringes for at least 20 passes. The resulting material was used between 30 seconds and 20 minutes after preparation. Prior to application, aliquots of 1 mL of the prepared FLOSEAL® material were dispensed into 3 mL syringes to provide an application volume of approximately 1 mL.

ARISTA™ AH (1 gram size) was used as supplied.

A series of two square lesions (approximately 1.0 cm×1.0 cm, and 0.2 to 0.3 cm deep) was created on the liver surface using sharp dissection. A metal die (1.0 cm×1.0 cm) was used to mark the outline of the lesion to be cut. While peeling back one corner with a forceps, the surface of the liver was incised, maintaining a thickness approximating the depth of the perimeter cuts. Each set of lesions was taken from the same relative location on the liver lobe. Lesion sets were taken initially from the distal region of the liver lobe and moved proximally on the liver lobe until the liver lobe was exhausted of accessible tissue area. At that time, another liver lobe was utilized. Each set of lesions and the lesion observation period were performed to completion before initiating another pair of lesions.

A qualitative assessment of bleeding was performed for each lesion prior to treatment, using a scale from 0 to 4 (0=no bleeding; 1=ooze or intermittent flow; 2=continuous flow; 3=controllable spurting and/or overwhelming flow; 4=unidentified or inaccessible spurting or gush) as described in Lewis et al., Surgery, vol. 161. no. 3, pp. 771-781 (2017).

To remove bias associated with potential differences in lesion severity, the individual applying articles to lesions did not know which lesion in any given set was to be treated with Powder Hemostat, FLOSEAL® VH S/D, or ARISTA™ AH until after both lesions were created and assessed.

Each lesion was blotted (as needed) to aid in assessment of the bleed grade. Powder Hemostat, FLOSEAL® VH S/D, and ARISTA™ AH were applied directly to the appropriate lesion and approximated with saline-moistened gauze for approximately 2 minutes. Lesions were treated with 0.6546±0.1196 g (mean±SD) Powder Hemostat, approximately 1 mL of the prepared FLOSEAL® VH S/D, and 0.7627±0.0551 g ARISTA™ AH.

A timer was started when the Powder Hemostat, FLOSEAL® VH S/D, or ARISTA™ AH was applied to the designated lesion. After removing digital pressure, each lesion was evaluated for hemostasis at 2, 3, 4, 5, 6, 7, and 10 minutes after application using the predefined scoring system discussed above. The lesion site was irrigated after the 10-minute hemostasis evaluation. The lesion site was then assessed if excess Powder Hemostat, FLOSEAL® VH S/D, or ARISTA™ AH material (material not incorporated in blood clot) was successfully irrigated away from the lesion site.

One primary endpoint of this study, hemostatic success at 10 minutes after application, was evaluated as the non-inferiority between Powder Hemostat and FLOSEAL® VH S/D, as well as superiority of Powder Hemostat over ARISTA™ AH. Non-inferiority between Powder Hemostat and FLOSEAL® VH S/D and superiority of Powder Hemostat over ARISTA™ AH was assessed in a hierarchical manner. A 90% two-sided confidence interval of the odds ratio of Powder Hemostat/FLOSEAL® VH S/D was calculated to assess non-inferiority between Powder Hemostat and FLOSEAL® VH S/D. A 95% two-sided confidence interval of the odds ratio of Powder Hemostat/ARISTA™ AH to test superiority was only calculated if and only if non-inferiority was concluded in the previous step. The choice of 90% and 95% two-sided confidence intervals for the evaluation of non-inferiority and superiority, respectively, corresponds to a 5% alpha level for each individual comparison. The hierarchical test principle guarantees the overall alpha level does not exceed 5%. The secondary endpoint of this study was time to hemostasis, which was interval-censored between the latest time point at which hemostatic success was not achieved and the subsequent time point at which hemostatic success was achieved and maintained.

The non-inferiority margin was set to 0.1776 based on a calculation using the Odds Ratio and Proportions Conversion Tool in PASS version 15.0.1, assuming a maximum acceptable loss of 15% efficacy and a 96% success rate. Since the 90% lower limit of the Confidence Interval ("CI") of the success odds ratio, 0.1824, was greater than the non-inferiority margin of 0.1776, hemostatic efficacy of Powder Hemostat was non-inferior to FLOSEAL® VH S/D 10 minutes after treatment. Concurrently, since the 95% lower limit of the CI of the success odds ratio, 7.3724, was greater than 1, Powder Hemostat proved to be superior over ARISTA™ AH. Time to hemostasis was 2.75 times longer with Powder Hemostat, compared with FLOSEAL® VH S/D (95% CI: 1.589 to 4.773, two-sided p-value <0.001), and 9.23 times longer with ARISTA™ AH as compared with Powder Hemostat (95% CI: 6.985 to 12.188, two-sided p-value <0.001).

Thus, under the conditions of the study, hemostatic efficacy of Powder Hemostat was non-inferior to FLOSEAL® VH S/D and superior to ARISTA™ AH in a heparinized porcine hepatic square bleeding model. Time to hemostasis, provided by Powder Hemostat, was 2.75 times as long as that provided by FLOSEAL® VH S/D and 9.23 times shorter than that provided by ARISTA™ AH.

Example 2—Degree of Swelling of Powder Hemostat

The degree of swelling of the Powder Hemostat granules described in Example 1 was determined. Upon contact with blood or other fluids, the particles swell up to 70% in diameter, with maximum swell volume achieved by about 10 minutes. In contrast, FLOSEAL® VH S/D particles (containing gelatin combined with thrombin) swelled approximately 10-20% in diameter upon contact with blood or other fluids, with the maximum swell volume achieved by about 10 minutes. The improved degree of swelling demonstrated by the Powder Hemostat granules advantageously facilitates hemostasis by applying force on the surrounding tissue, thereby providing an enhanced mechanical tamponade effect.

Example 3—Powder Expression

Using one or more of the above described methods of using the spring cap assembly 120, the efficiency and predictability of powder expression in sequential expressions was evaluated.

System 100 was used to illustrate functional expression of a powder polymeric agent across five expressions. Syringe 110 was prefilled with a powder polymeric agent between 0.5 g to 2.5 g, with a preferred fill within 1.3 g to 1.4 g. The results of the powder expression testing are shown in the chart illustrated in FIG. 15. To control for consistent expression of powder in sequential expressions, the system 100 was oriented with a delivery angle between 90 to 45 degrees, with a preferable angle of 90 degrees (vertical).

Figure 15:
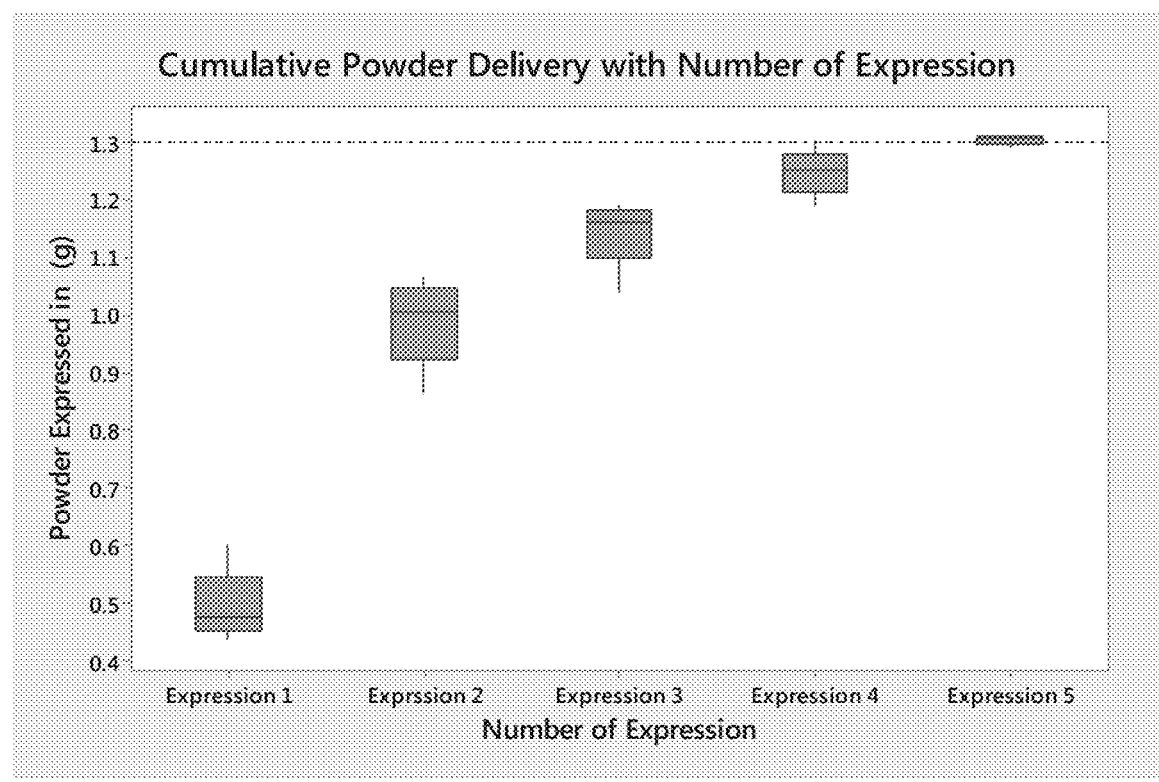
FIG. 15 illustrates a chart plotting cumulative powder delivery with number of expressions for one example embodiment of the present disclosure

Referring now to FIG. 15, the quantities of the powder expressed in cumulative grams were measured between each expression. The total gram quantity expressed is plotted along the vertical axis with the sequential expression plotted along the horizontal axis. A dashed line indicates the lower limit of the preferred fill range discussed above (1.3 g to 1.4 g). When the cumulative quantity of powder expressed exceeds the dashed line, an acceptable full expression of material has been achieved. In the illustrated example, the system 100 delivers greater than 95% of the powder within five expressions.

It should be appreciated that, as discussed above, the system 100 may be modified to allow a user to more flexibly control the quantity of product to be delivered. In various embodiments, the system 100 may be modified with a check valve to express a controllably smaller quantity of material with each plunger depression. In other various embodiments, the system 100 may be outfitted with an expanded or restricted orifice or a modified plunger length to alter the number of expressions necessary to deliver a full quantity of material. The amount of material delivered can cover an area of between 1 $cm^2$ and 5 $cm^2$ with an average area of 3 $cm^2$.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A snap-fit adapter for mountably converting a hemostatic powder syringe into an intermittent spray powder dispensing syringe delivery device, the hemostatic powder syringe including a barrel having a distal end with a discharge opening, a proximal end with outwardly extending finger flanges, a plunger having a distal end with a stopper slideably received in the barrel and a flanged proximal end with a receptacle, and a hemostatic powder disposed in said barrel between the discharge opening and the stopper, the snap-fit adapter comprising:
   a coil spring having a first end and an opposed second end;
   a retainer ring including a central opening and an inner peripheral wall having a plurality of clips extending from the peripheral wall and receiving one ring circle of the first end of the spring; and
   a cap having a generally cylindrical configuration including a closed top with an inner facing surface and an upstanding peripheral sidewall, a central post projecting from the inner surface, a plurality of projecting members extending inwardly from the inner surface terminating in raised step surfaces disposed between the post and the peripheral sidewall, and a plurality of resilient latch arms having a first end extending from said inner surface and disposed between the projecting members and the peripheral sidewall to an opposed free second end spaced from the first end, each free end including a cam surface and a latch surface facing the inner surface of the cap positioned adjacent to a raised step surface, the cap further including a plurality of clips extending from the peripheral sidewall for receiving one ring circle of the second end of the spring,
   whereby the snap fit adapter may be pushed onto the proximal end of the plunger so that the post is received in the receptacle and the proximal end flange is securely retained between the raised step surfaces and the latch surfaces and the retainer ring rests against the finger flanges of the barrel with the spring biasing the cap away from the retainer ring and such that the adapter is reciprocally movable between a compressed position wherein the cap is moved toward the retainer ring and the spring is compressed thereby translating the plunger toward the distal end of the syringe, and a relaxed position where the cap is moved away from the retainer ring and the spring is relaxed thereby translating the plunger toward the proximal end of the syringe, and whereby repeated movement of the cap between the relaxed position and the compressed position is effective to intermittently spray the hemostatic powder from the discharge opening.

2. A snap-fit adapter as defined in claim 1, wherein the post extends along an axis of the spring towards the retainer ring and is disposed concentrically within the spring.

3. A snap fit adapter as defined in claim 1, wherein the post, raised surfaces and latch arms are integrally formed with the cap.

4. A snap-fit adapter as defined in claim 1, wherein the spring has a spring constant of 1 to 10 pounds force.

5. A snap-fit adapter as defined in claim 1, wherein the spring comprises stainless steel wire.

6. A snap-fit adapter as defined in claim 1, wherein said clips define openings through which the respective ends of the spring are received.

7. A snap-fit adapter as defined in claim 1, wherein said clips securely affix the opposed ends of the spring to the cap and the retention ring respectively, to prevent axial rotation.

8. A snap-fit adapter as defined in claim 1, where a difference in relative heights of the latch surfaces and the raised step surfaces defines a gap having approximately the same thickness as the thickness of the flange of the proximal end of the plunger to securely retain the cap onto the plunger of the syringe.

9. A method for intermittently spraying a hemostatic powder from a hemostatic powder syringe, said method comprising: providing a hemostatic powder syringe including a barrel having a distal end with a discharge opening, a proximal end with outwardly extending finger flanges, a plunger having a distal end with a stopper slideably received in the barrel and a flanged proximal end with a receptacle, and a hemostatic powder disposed in said barrel between the discharge opening and the stopper; providing a snap-fit adapter including: a coil spring having a first end and an opposed second end; a retainer ring including a central opening and an inner peripheral wall having a plurality of clips extending from the peripheral wall and receiving one ring circle of the first end of the spring; and a cap having a generally cylindrical configuration including a closed top with an inner facing surface and an upstanding peripheral sidewall, a central post projecting from the inner surface, a plurality of projecting members extending inwardly from the inner surface terminating in raised step surfaces disposed between the post and the peripheral sidewall, and a plurality of resilient latch arms having a first end extending from said inner surface and disposed between the projecting members and the peripheral sidewall to an opposed free second end spaced from the first end, each free end including a cam surface and a latch surface facing the inner surface of the cap positioned adjacent to a raised step surface, the cap further including a plurality of clips extending from the peripheral sidewall for receiving one ring circle of the second end of the spring, mounting the snap-fit adapter onto the syringe by pushing the snap fit adapter onto the proximal end of the plunger so that the post is received in the receptacle and the proximal end flange is securely retained between the raised step surfaces and the latch surfaces and the retainer ring rests against the finger flanges of the barrel with the spring biasing the cap away from the retainer ring; and reciprocally moving the snap-fit adapter between a compressed position wherein the cap is moved toward the retainer ring and the spring is compressed thereby translating the plunger toward the distal end of the syringe, and a relaxed position where the cap is moved away from the retainer ring and the spring is relaxed thereby translating the plunger toward the proximal end of the syringe, and such that repeated movement of the cap between the relaxed position and the compressed position is effective to intermittently spray the hemostatic powder from the discharge opening.

10. A method as defined in claim 9, wherein the hemostatic powder comprises dry particles of crosslinked bovine gelatin and non-crosslinked bovine gelatin.

11. A method as defined in claim 9, wherein the hemostatic powder is sprayed onto a bleeding wound with the syringe barrel oriented at a delivery angle of between 90 to 45 degrees with respect to the wound.

12. A kit comprising: a hemostatic powder syringe including a barrel having a distal end with a discharge opening, a proximal end with outwardly extending finger flanges, a plunger having a distal end with a stopper slideably received in the barrel and a flanged proximal end with a receptacle, and a hemostatic powder disposed in said barrel between the discharge opening and the stopper; and a snap-fit adapter comprising: a coil spring having a first end and an opposed second end; a retainer ring including a central opening and an inner peripheral wall having a plurality of clips extending from the peripheral wall and receiving one ring circle of the first end of the spring; and a cap having a generally cylindrical configuration including a closed top with an inner facing surface and an upstanding peripheral sidewall, a central post projecting from the inner surface, a plurality of projecting members extending inwardly from the inner surface terminating in raised step surfaces disposed between the post and the peripheral sidewall, and a plurality of resilient latch arms having a first end extending from said inner surface and disposed between the projecting members and the peripheral sidewall to an opposed free second end spaced from the first end, each free end including a cam surface and a latch surface facing the inner surface of the cap positioned adjacent to a raised step surface, the cap further including a plurality of clips extending from the peripheral sidewall for receiving one ring circle of the second end of the spring, whereby for use, the snap fit adapter may be pushed onto the proximal end of the plunger so that the post is received in the receptacle and the proximal end flange is securely retained between the raised step surfaces and the latch surfaces and the retainer ring rests against the finger flanges of the barrel with the spring biasing the cap away from the retainer ring and such that the adapter is reciprocally movable between a compressed position wherein the cap is moved toward the retainer ring and the spring is compressed thereby translating the plunger toward the distal end of the syringe, and a relaxed position where the cap is moved away from the retainer ring and the spring is relaxed thereby translating the plunger toward the proximal end of the syringe, and whereby repeated movement of the cap between the relaxed position and the compressed position is effective to intermittently spray the hemostatic powder from the discharge opening; and instructions for use.

* * * * *